(12) United States Patent
Katayama

(10) Patent No.: US 6,650,129 B1
(45) Date of Patent: Nov. 18, 2003

(54) METHOD OF TESTING SEMICONDUCTOR DEVICE

(75) Inventor: Toshiharu Katayama, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/271,540

(22) Filed: Oct. 17, 2002

(30) Foreign Application Priority Data

May 13, 2002 (JP) ........................................ 2002-137261

(51) Int. Cl.$^7$ ............................................ G01R 31/305

(52) U.S. Cl. ..................... 324/751; 324/752; 250/310; 250/492.2

(58) Field of Search ...................... 324/71.3, 750–754, 324/501, 158.1; 250/310, 307, 397, 492.2; 356/237.1, 334, 376, 394

(56) References Cited

U.S. PATENT DOCUMENTS

| | | | | |
|---|---|---|---|---|
| 4,902,967 A | * | 2/1990 | Flesner | 324/751 |
| 6,038,018 A | * | 3/2000 | Yamazaki et al. | 356/237.1 |
| 6,344,750 B1 | * | 2/2002 | Lo et al. | 324/751 |

* cited by examiner

*Primary Examiner*—Ernest Karlsen
*Assistant Examiner*—Minh N. Tang
(74) *Attorney, Agent, or Firm*—Oblon, Spivak, McClelland, Maier & Neustadt, P.C.

(57) ABSTRACT

A method of testing a semiconductor device is provided. In a SEM image comparison type testing apparatus, a comparison is made between the voltage contrast of a predetermined pattern to be tested and the voltage contrast of a reference pattern to produce a comparison image containing only one of two binary contrast levels. A dimension based on contrast regions in the comparison image is measured, and a characterizing dimension varying depending on the process of manufacture of the semiconductor device is analyzed from the result of measurement.

19 Claims, 22 Drawing Sheets

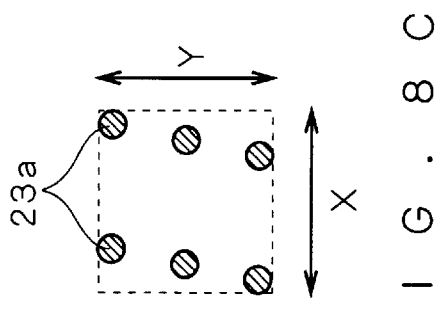
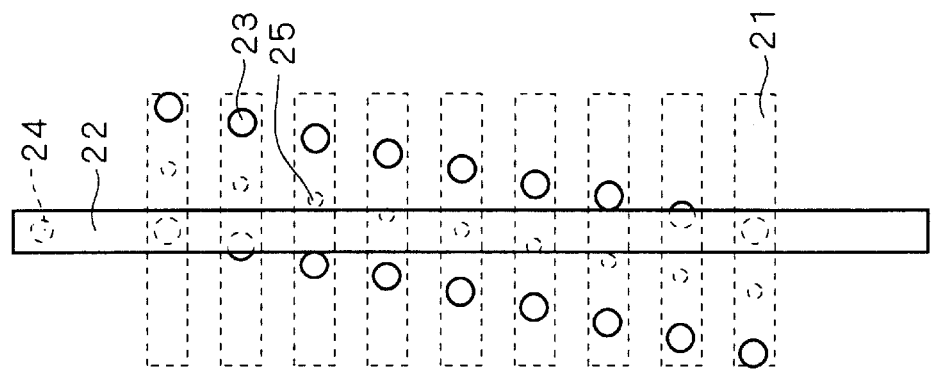
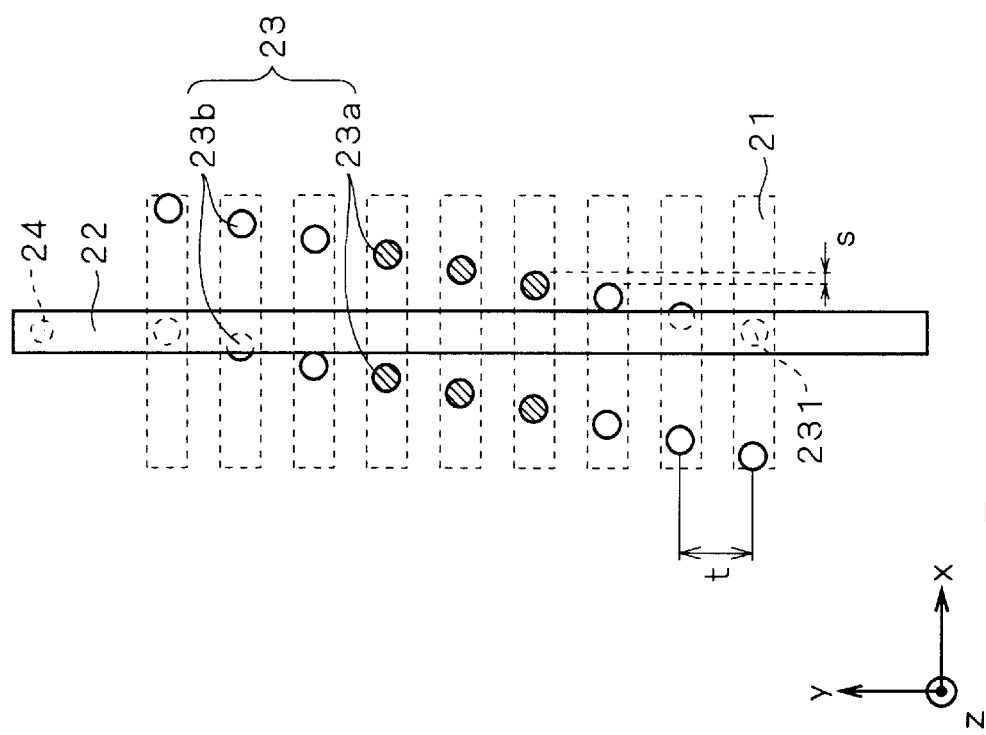

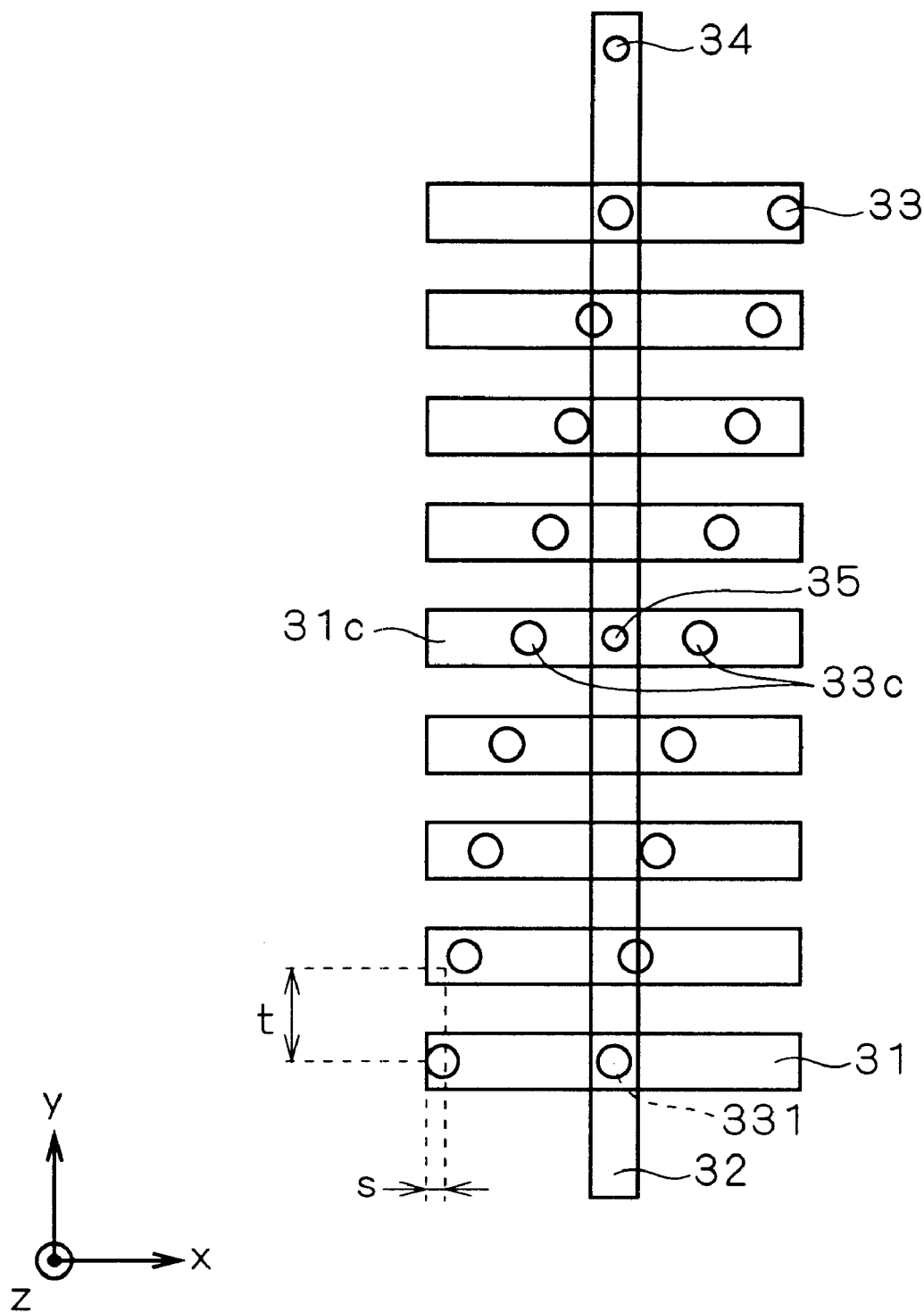

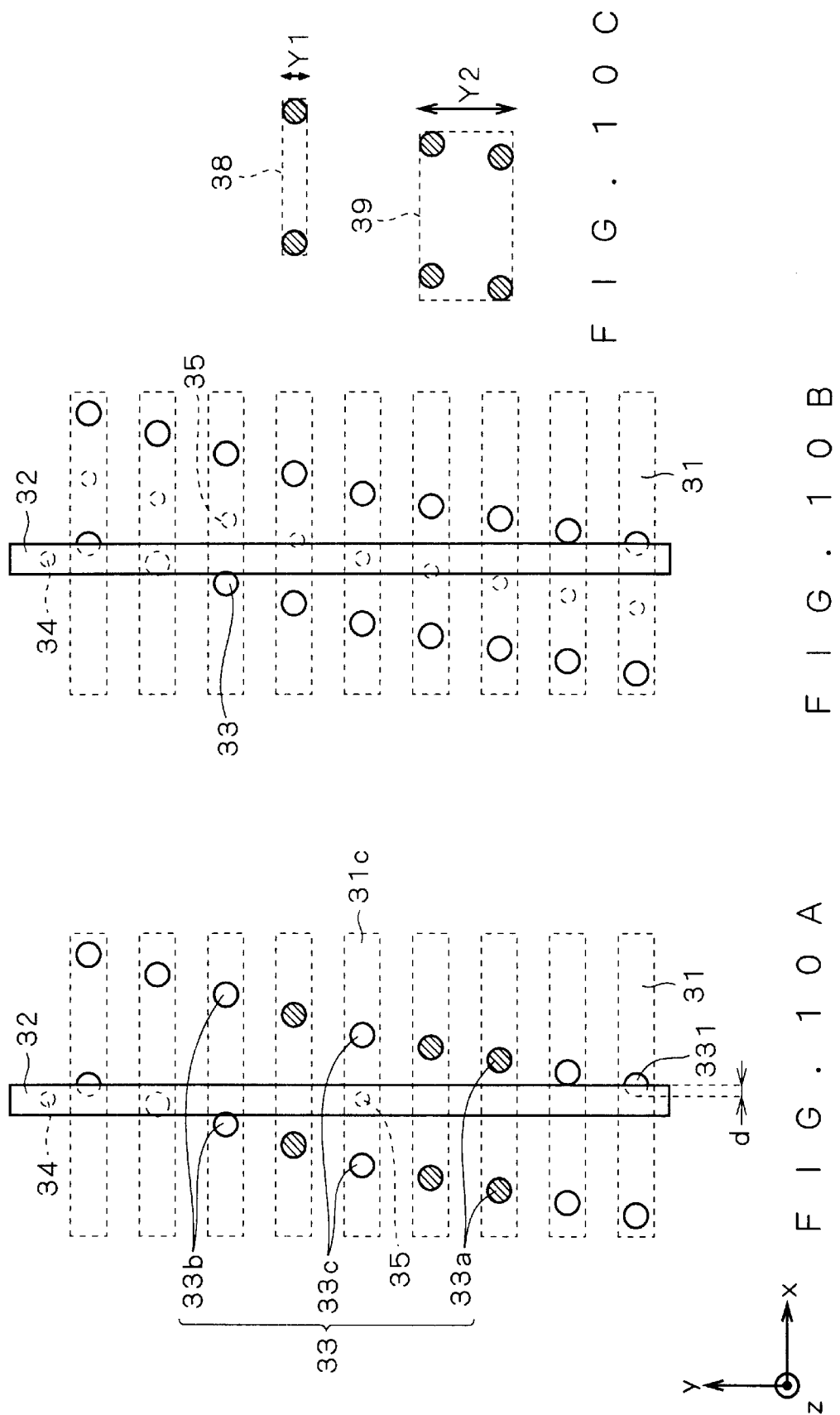

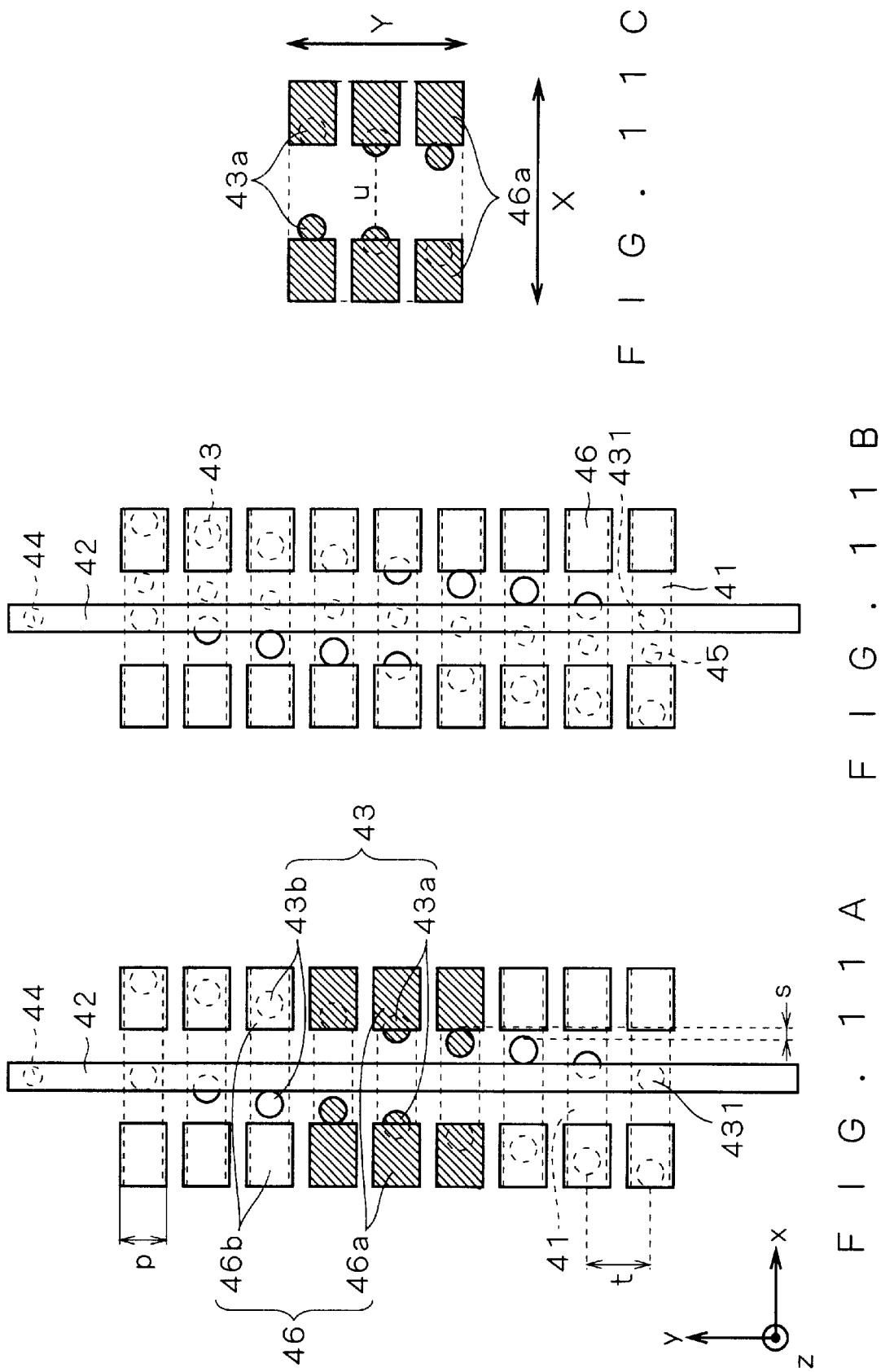

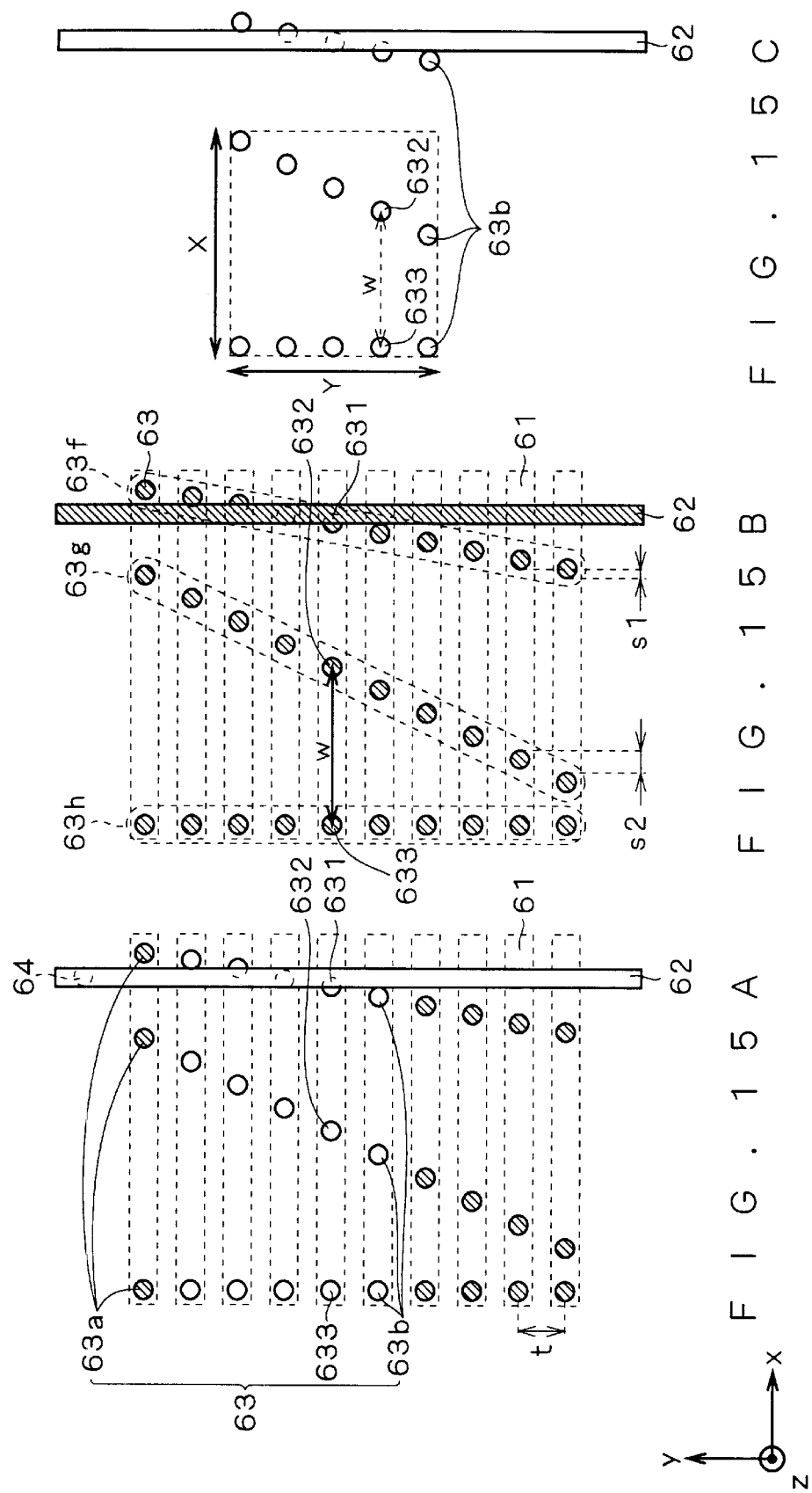

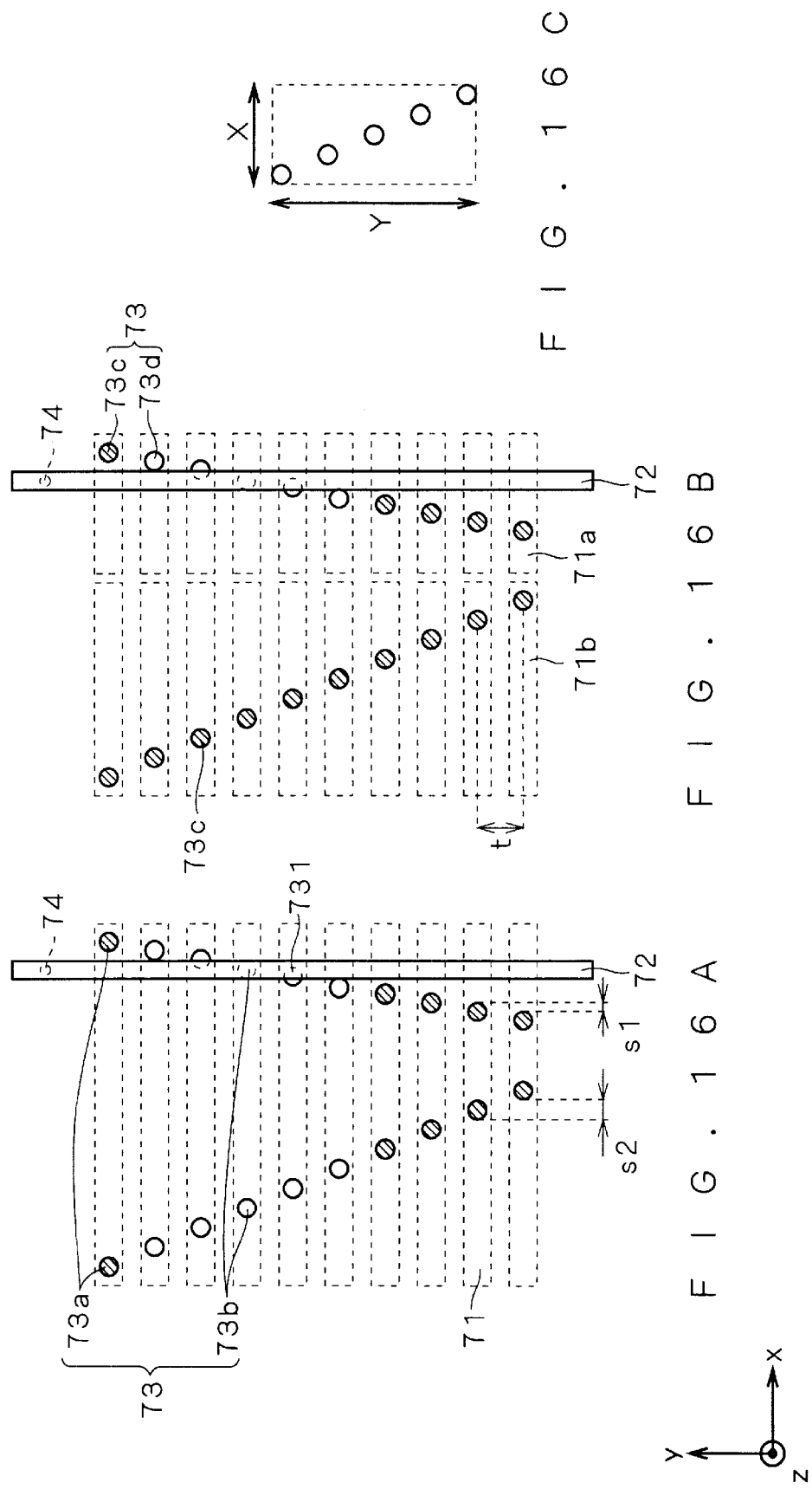

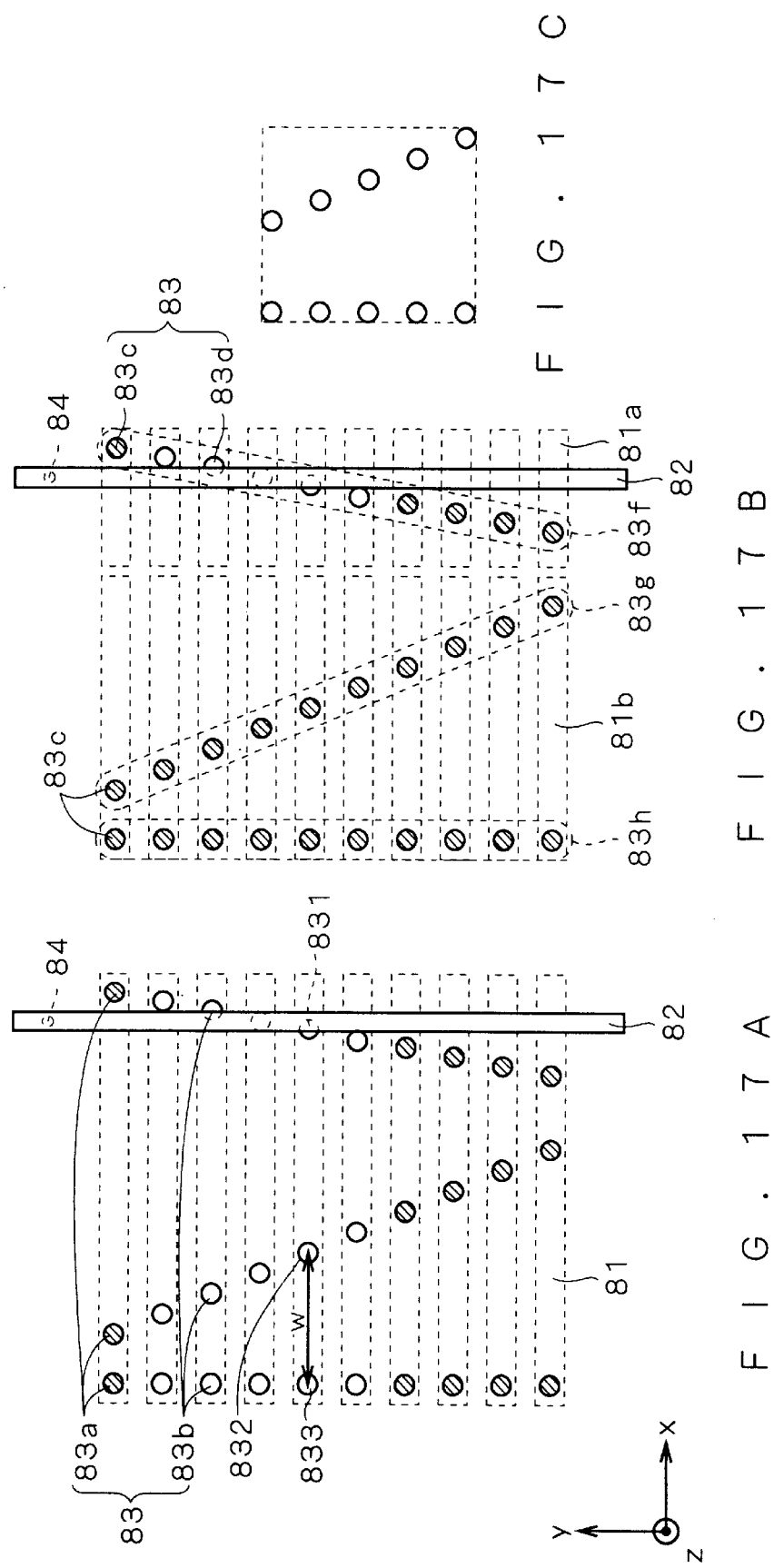

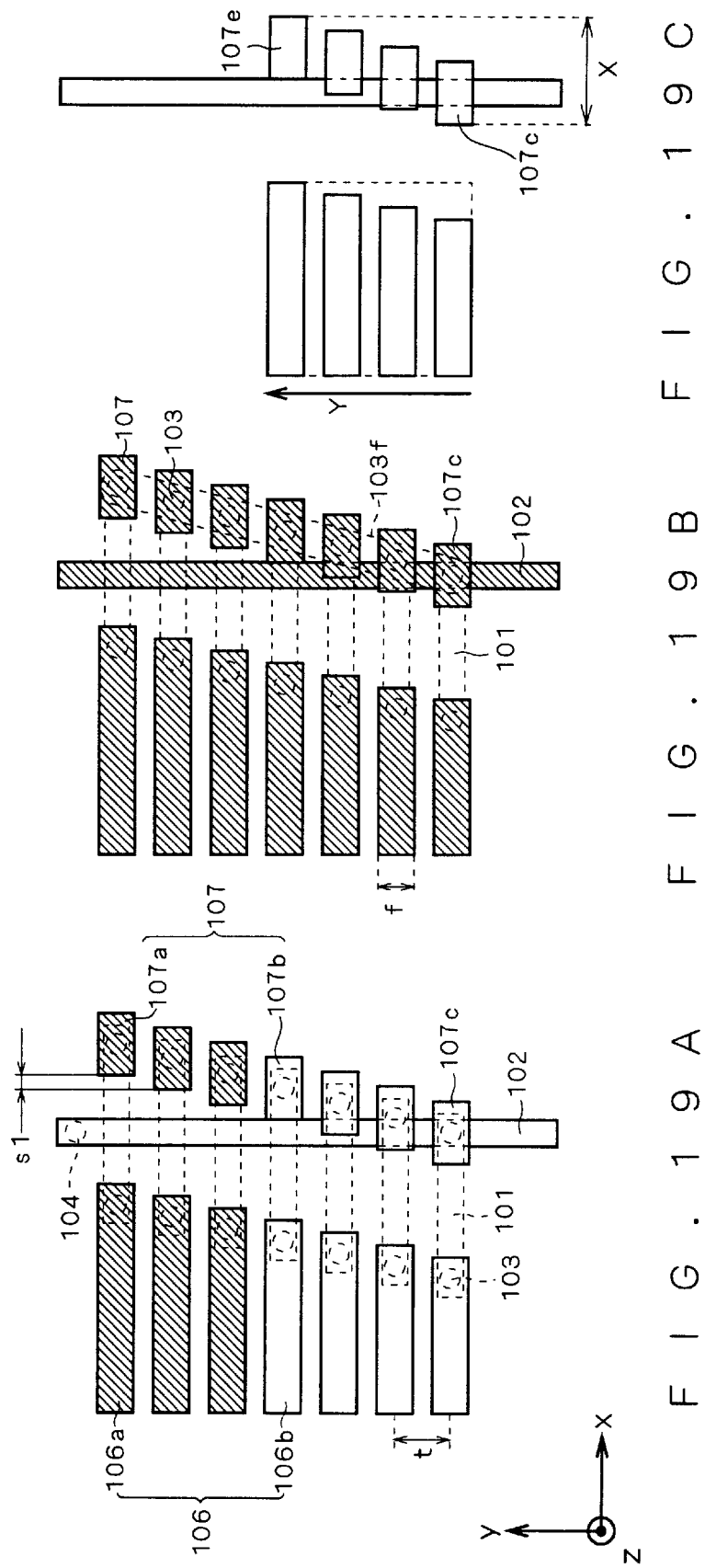

METHOD OF TESTING SEMICONDUCTOR DEVICE

BACKGROUND OF THE INVENTION

1. Field of the Invention

The present invention relates to a method of testing a semiconductor device. More particularly, the invention relates to a method of testing a semiconductor device which measures characterizing dimensions such as a via covering amount, a misalignment amount and a short margin in the course of the manufacture of the semiconductor device.

2. Description of the Background Art

Conventionally, tests have been conducted as appropriate on semiconductor devices in the course of the manufacture of the semiconductor devices for the purpose of maintaining the quality of products or detecting manufacturing failures in an early stage. An example of the methods of such tests includes measuring a connection (a via covering amount) of an upper-level interconnect line to a via plug, a short margin between interconnect lines and the like, which exhibit variations particularly in the course of manufacture. This method employs a scanning electron microscope (SEM) and an overlay measurement apparatus using an optical technique in combination.

A background art method of testing a semiconductor device for poor connection of an upper-level interconnect line to a via plug is described. FIG. 23 is a sectional view showing the design of a semiconductor device. FIG. 24 is a sectional view of a semiconductor device actually manufactured based on the design of FIG. 23.

In FIGS. 23 and 24, the reference numeral 1 designates a lower-level interconnect line; 2 designates an interlayer insulation film; 4 designates an upper-level interconnect line; and 3 designates a via plug for electrical connection between the lower-level interconnect line 1 and the upper-level interconnect line 4. Reference character a designates a via covering amount; b designates a via plug diameter; c designates an upper-level interconnect line width; b' designates the design value of the via plug diameter; a' designates the design value of the via covering amount; c' designates the design value of the upper-level interconnect line width; d' designates the design value of a misalignment amount (or a distance between the center of the via plug diameter b' and the center of the upper-level interconnect line width c'); and d is a misalignment amount, that is, the amount of misalignment from the design value d' which occurs during actual pattern formation. Thus, d+d' is an actually formed distance between the center of the via plug diameter b and the center of the upper-level interconnect line width c.

The via covering amount a' is defined during the design phase in a manner to be described below. The end of the upper-level interconnect line 4 which is closer to the central axis of the via plug 3 is referred to as a first end, and the end of the via plug 3 on the opposite side from the first end is referred to as a second end. Then, the via covering amount a' is a distance between the first end and the second end (See FIG. 23).

The via covering amount a is a distance between the first and second ends defined when the above-mentioned design is prepared (See FIG. 24).

A conventional method of examining the via covering amount a of the upper-level interconnect line 4 with respect to the via plug 3 is described with reference to FIGS. 23 and 24.

Referring to FIG. 23, the via covering amount a' of the upper-level interconnect line 4 with respect to the via plug 3 is given by $$a'=(b'+c')/2-d' \qquad (1)$$

On the other hand, with reference to FIG. 24, the via covering amount a of the upper-level interconnect line 4 with respect to the via plug 3 is similarly given by $$a=(b+c)/2-(d'+d) \qquad (2)$$

Subtracting Equation (1) from Equation (2) provides $$a=a'+(b-b')/2+(c-c')/2\pm d \qquad (3)$$

which is an equation for the via covering amount a when the semiconductor device is actually manufactured. In Equation (3), the sign in front of "d" is "minus" when the center of the actually formed upper-level interconnect line 4 is misaligned leftwardly from the center of the upper-level interconnect line 4 in the design phase, and is "plus" when it is misaligned rightwardly.

Thus, the via covering amount a of the upper-level interconnect line 4 with respect to the via plug 3 is determined indirectly from Equation (3) by measuring the via plug diameter b and the upper-level interconnect line width c by means of the SEM and measuring the misalignment amount d by means of the overlay measurement apparatus using the optical technique.

In this manner, the background art method has measured the via cover amount a to test for poor connection of the upper-level interconnect line to the via plug.

A background art test for a failure between adjacent interconnect lines has been conducted by directly measuring a short margin between adjacent upper-level interconnect lines 4 by means of the SEM.

However, the overlay measurement apparatus employing the optical technique for use in determination of the via covering amount a is not capable of reducing errors to a negligible level due to the performance thereof to fail to measure the via covering amount a with high accuracy because of the errors. Therefore, the overlay measurement apparatus is not capable of conducting a test for poor connection of the upper-level interconnect line 4 to the via plug 3 accurately.

Measuring the short margin between the upper-level interconnect lines 4 presents no problem if the upper-level interconnect lines 4 have a uniform width as shown in FIG. 25. In actual manufacture, however, the upper-level interconnect lines 4 have a taper (or inclination) as shown in FIG. 26. Specifically, the upper-level interconnect lines 4 have a bottom width c2 greater than a top width c1. If the upper-level interconnect lines 4 have the above-mentioned taper and a high aspect ratio, the above-mentioned SEM testing method is not capable of observing the bottom width c2.

In a damascene structure shown in FIG. 27, the bottom of the upper-level interconnect lines 4 is formed inside the interlayer insulation film 2. Thus, the above-mentioned SEM testing method also is not capable of observing the bottom width c2.

In the instances shown in FIGS. 26 and 27, the testing method for failure between the upper-level interconnect lines 4 is not capable of measuring the short margin between the upper-level interconnect lines 4 with high accuracy to find it difficult to conduct a test for failure between the interconnect lines accurately.

SUMMARY OF THE INVENTION

It is an object of the present invention to provide a method of testing a semiconductor device which is capable of accurately measuring a via covering amount of an upper-level interconnect line with respect to a via plug, a short margin between (upper-level) interconnect lines and the like which exhibit process variations.

The present invention is intended for a method of testing a semiconductor device being manufactured on a semiconductor substrate by detecting secondary electrons produced by irradiation of a predetermined region with a primary electron beam and using a voltage contrast produced based on the intensity of the secondary electrons. According to the present invention, the method includes the following steps (a) through (h). The step (a) is to prepare a predetermined pattern to be tested. The step (b) is to prepare a reference pattern similar in construction to the predetermined pattern. The step (c) is to produce the voltage contrast of the predetermined pattern. The step (d) is to produce the voltage contrast of the reference pattern. The step (e) is to make a comparison between the voltage contrast of the predetermined pattern and the voltage contrast of the reference pattern to produce a first comparison image, and to binarize the first comparison image. The step (f) is to produce a second comparison image containing only one of two binary contrast levels resulting from the binarization in the step (e). The step (g) is to measure a dimension based on the second comparison image. The step (h) is to determine a characterizing dimension varying depending on the process of manufacture of the semiconductor device from a result of measurement in the step (g).

Designing a test pattern for the predetermined pattern to be tested and the like minimizes measurement errors. Production and binarization of the first comparison image facilitates the measurement of the dimension based on the contrast regions, to allow automatic testing depending on settings, thereby preventing human error.

These and other objects, features, aspects and advantages of the present invention will become more apparent from the following detailed description of the present invention when taken in conjunction with the accompanying drawings.

BRIEF DESCRIPTION OF THE DRAWINGS

FIG. 8A shows the construction and voltage contrast of a pattern to be tested according to the second preferred embodiment;

FIG. 8B shows the construction and voltage contrast of a reference pattern according to the second preferred embodiment;

FIG. 8C shows a comparison image according to the second preferred embodiment;

FIG. 9 shows a test pattern in the design phase according to a third preferred embodiment of the present invention;

FIG. 10A shows the construction and voltage contrast of a pattern to be tested according to the third preferred embodiment;

FIG. 10B shows the construction and voltage contrast of a reference pattern according to the third preferred embodiment;

FIG. 10C shows a comparison image according to the third preferred embodiment;

FIG. 11A shows the construction and voltage contrast of a pattern to be tested according to a fourth preferred embodiment of the present invention;

FIG. 11B shows the construction and voltage contrast of a reference pattern according to the fourth preferred embodiment;

FIG. 11C shows a comparison image according to the fourth preferred embodiment;

FIG. 15A shows the construction and voltage contrast of a pattern to be tested according to the sixth preferred embodiment;

FIG. 15B shows the construction and voltage contrast of a reference pattern according to the sixth preferred embodiment;

FIG. 15C shows a comparison image according to the sixth preferred embodiment;

FIG. 16A shows the construction and voltage contrast of a pattern to be tested according to a seventh preferred embodiment of the present invention;

FIG. 16B shows the construction and voltage contrast of a reference pattern according to the seventh preferred embodiment;

FIG. 16C shows a comparison image according to the seventh preferred embodiment;

FIG. 17A shows the construction and voltage contrast of a pattern to be tested according to an eighth preferred embodiment of the present invention;

FIG. 17B shows the construction and voltage contrast of a reference pattern according to the eighth preferred embodiment;

FIG. 17C shows a comparison image according to the eighth preferred embodiment;

FIG. 19A shows the construction and voltage contrast of a pattern to be tested according to a tenth preferred embodiment of the present invention;

FIG. 19B shows the construction and voltage contrast of a reference pattern according to the tenth preferred embodiment;

FIG. 19C shows a comparison image according to the tenth preferred embodiment;

DESCRIPTION OF THE PREFERRED EMBODIMENTS

Figure 1:
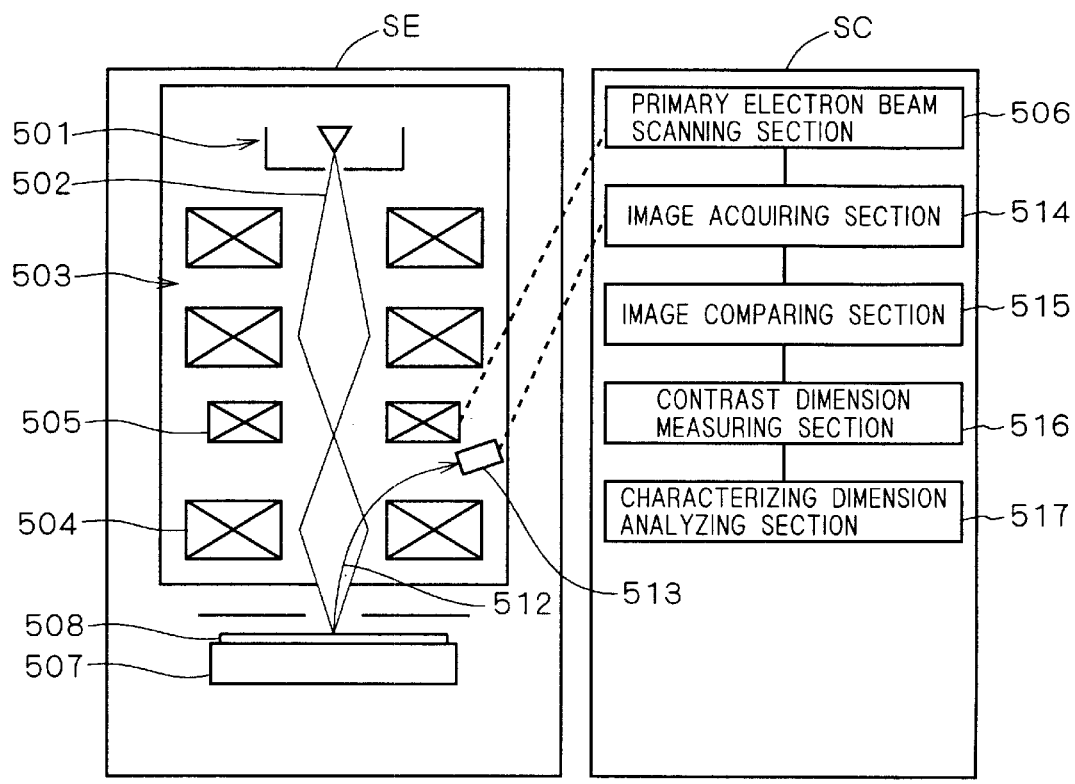
FIG. 1 schematically shows a construction of a SEM image comparison type testing apparatus according to the present invention.

The present invention will now be specifically described with reference to the drawings illustrating preferred embodiments of the invention. Reference numerals and characters identical with those of the background art are used to designate identical or equivalent members and variables. The via covering amount a, the misalignment amount d and a variable e used for designating a short margin between interconnect lines (the variable e is a distance between the top ends of adjacent interconnect lines at the instant when bottom ends thereof come into contact with each other and is referred to hereinafter as a top-to-top distance) according to the present invention are referred to generically as characterizing dimensions.

The present invention employs a SEM image comparison type testing apparatus based on a scanning electron microscope (SEM) which is capable of detecting not only pattern defects but also potential failure defects (potential contrast defects) found from a potential contrast difference and the like. FIG. 1 schematically shows a construction of a SEM image comparison type testing apparatus 500.

<Apparatus Construction>

As shown in FIG. 1, the SEM image comparison type testing apparatus 500 comprises a SEM main body SE and a controller SC for controlling components of the SEM main body SE.

The SEM main body SE includes an electron gun 501; a condenser lens 503 for collecting a primary electron beam 502 emitted from the electron gun 501; an objective lens 504 for focusing the primary electron beam 502 into one spot on a sample; a deflector 505 for scanning the primary electron beam 502; a stage 507 for placing the sample thereon; and a secondary electron detector 513 for detecting secondary electrons 512 emitted from the sample. A semiconductor device 508 is placed as the sample on the stage 507.

The controller SC includes a primary electron beam scanning section 506 for controlling the deflector 505 to scan the primary electron beam 502; an image acquiring section 514 for receiving an output from the secondary electron detector 513; an image comparing section 515 for comparing voltage contrasts acquired by the image acquiring section 514; a contrast dimension measuring section 516 for measuring a dimension based on contrast regions in a comparison image produced by the image comparing section 515; and a characterizing dimension analyzing section 517 for analyzing a characterizing dimension, such as the via covering amount a, based on a result of measurement by the contrast dimension measuring section 516.

<Apparatus Operation>

Fundamental operation of the SEM image comparison type testing apparatus 500 will be described with reference to FIG. 1.

The primary electron beam 502 emitted from the electron gun 501 is directed through the condenser lens 503 and the objective lens 504 onto a pattern to be tested on the semiconductor device 508.

The deflector 505 controlled by the primary electron beam scanning section 506 scans the primary electron beam 502 over the semiconductor device 508. In synchronism with the scanning, the secondary electron detector 513 receives the secondary electrons 512 emitted from the semiconductor device 508 in response to the primary electron beam 502 directed onto the semiconductor device 508.

The image acquiring section 514 receives the secondary electrons 512 received by the secondary electron detector 513 in the form of a secondary electron intensity. The image acquiring section 514 performs intensity modulation upon the secondary electron intensity to produce a voltage contrast of the pattern to be tested.

Next, the area to be tested is changed to a reference pattern formed on the same semiconductor device 508, and similar processing is performed on the reference pattern. Thus, the image acquiring section 514 produces the voltage contrast of the reference pattern.

The image comparing section 515 makes a contrast comparison between the voltage contrast of the pattern to be tested and the voltage contrast of the reference pattern to produce a first comparison image. Also, the image comparing section 515 binarizes the contrast of the first comparison image to produce a second comparison image containing only one of two binary contrast levels (bright or dark) resulting from the binarization.

The contrast dimension measuring section 516 measures a dimension based on contrast regions in the second comparison image produced by the image comparing section 515 by using a clustering function and a dimension measuring function. Specifically, if there are a plurality of contrast regions in the second comparison image, the contrast dimension measuring section 516 uses the clustering function to recognize necessary contrast regions as a cluster, and uses the dimension measuring function to measure the size of the cluster.

Since the voltage contrasts and the first and second comparison images are in digital form, easy setting allows the image comparing section 515 to automatically carry out the production of the first comparison image, the binarization of the first comparison image and the production of the second comparison image, and allows the contrast dimension measuring section 516 to automatically carry out the contrast dimension measuring and clustering processes.

Thereafter, the characterizing dimension analyzing section 517 automatically analyzes the dimension based on the contrast regions in the second comparison image, which is measured by the contrast dimension measuring section 516, to derive the characterizing dimension (e.g., the via covering amount a).

Figure 2:
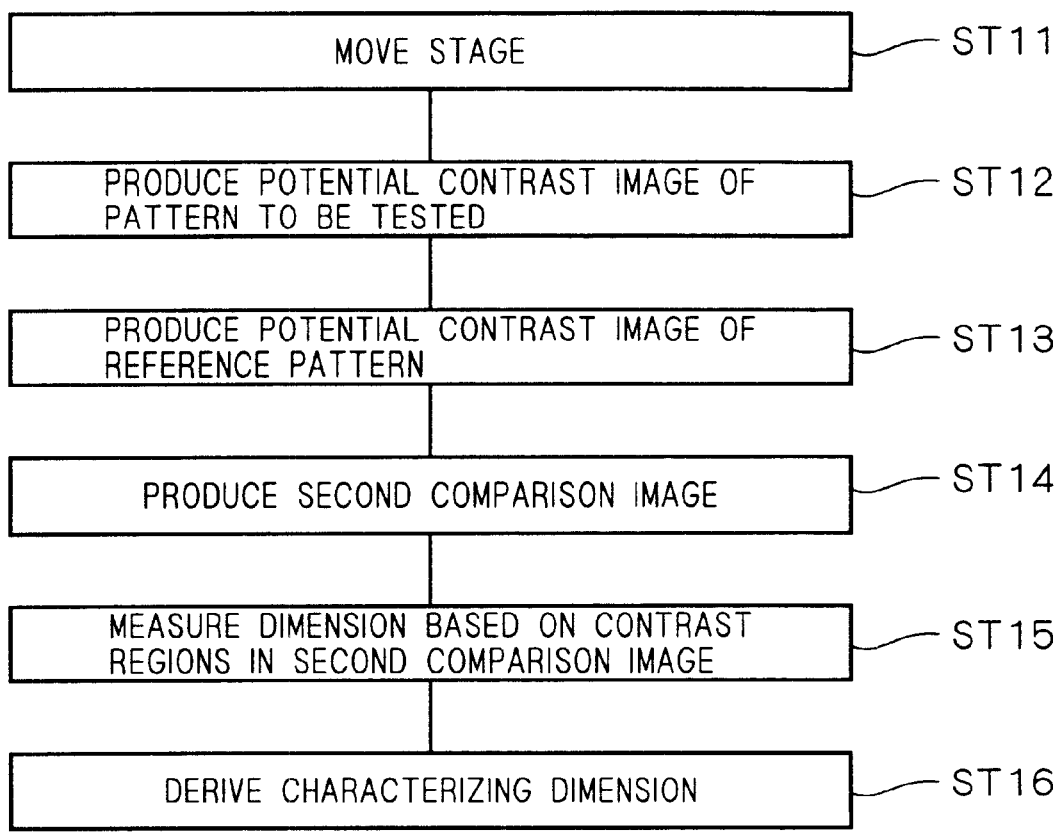
FIG. 2 is a flowchart showing a flow of a series of process steps in a method of testing a semiconductor device according to the present invention.

A flow of processes of operation of the SEM image comparison type testing apparatus 500 will be described with reference to the flowchart of FIG. 2.

First, the stage 507 is moved so that the primary electron beam 502 impinges upon the semiconductor device 508 (Step ST11).

Next, a pattern region to be tested on the semiconductor device 508 is scanned with the primary electron beam 502, and the secondary electron detector 513 detects the secondary electrons 512 emitted from the pattern region, whereby the voltage contrast of the pattern to be tested is produced (in Step ST12).

Next, a reference pattern region on the semiconductor device 508 is scanned with the primary electron beam 502, and the secondary electron detector 513 detects the secondary electrons 512 emitted from the reference pattern region, whereby the voltage contrast of the reference pattern is produced (Step ST13).

Then, the image comparing section 515 makes the contrast comparison between the voltage contrast of the pattern to be tested and the voltage contrast of the reference pattern to produce the first comparison image. The image comparing section 515 binarizes the first comparison image to produce the second comparison image containing only one of the two binary contrast levels resulting from the binarization (Step ST14).

The contrast dimension measuring section 516 measures a dimension based on the contrast regions in the second comparison image (Step ST15).

Finally, the characterizing dimension analyzing section 517 analyzes and derives the characterizing dimension (such as the via covering amount a) from the dimension based on the contrast regions which is measured in Step ST15 (Step ST16).

Specific description will be given on a method of testing a semiconductor device by measuring the via covering amount a and the misalignment amount d of an upper-level interconnect line with respect to a via plug formed in the semiconductor device 508, the top-to-top distance e, or the like by using the SEM image comparison type testing apparatus 500 having the above-mentioned functions according to preferred embodiments of the present invention.

<First Preferred Embodiment>

Figure 3:
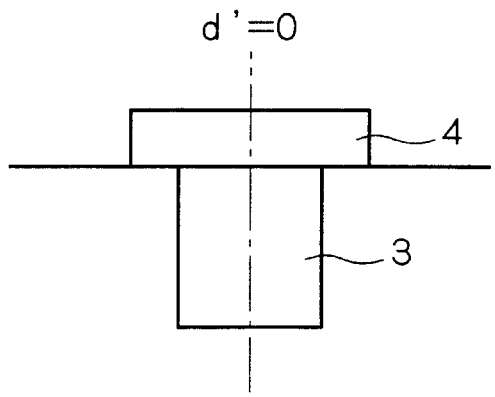
FIG. 3 is a sectional view of a via plug and an upper-level interconnect line the respective centers of which coincide with each other in the design phase.

A first preferred embodiment of the present invention is intended to measure the via covering amount a of an upper-level interconnect line with respect to a via plug with high accuracy. More specifically, the first preferred embodiment is intended to accurately determine the via covering amount a and the misalignment amount d of the upper-level interconnect line 4 with respect to a via plug 3 actually formed in the semiconductor device 508, based on d'=0 (indicating that the center of the diameter of the via plug 3 coincides with the center of the width of the upper-level interconnect line 4) designed in the design phase, as shown in FIG. 3. For this purpose, a test structure shown in FIG. 4 is designed.

Figure 4:
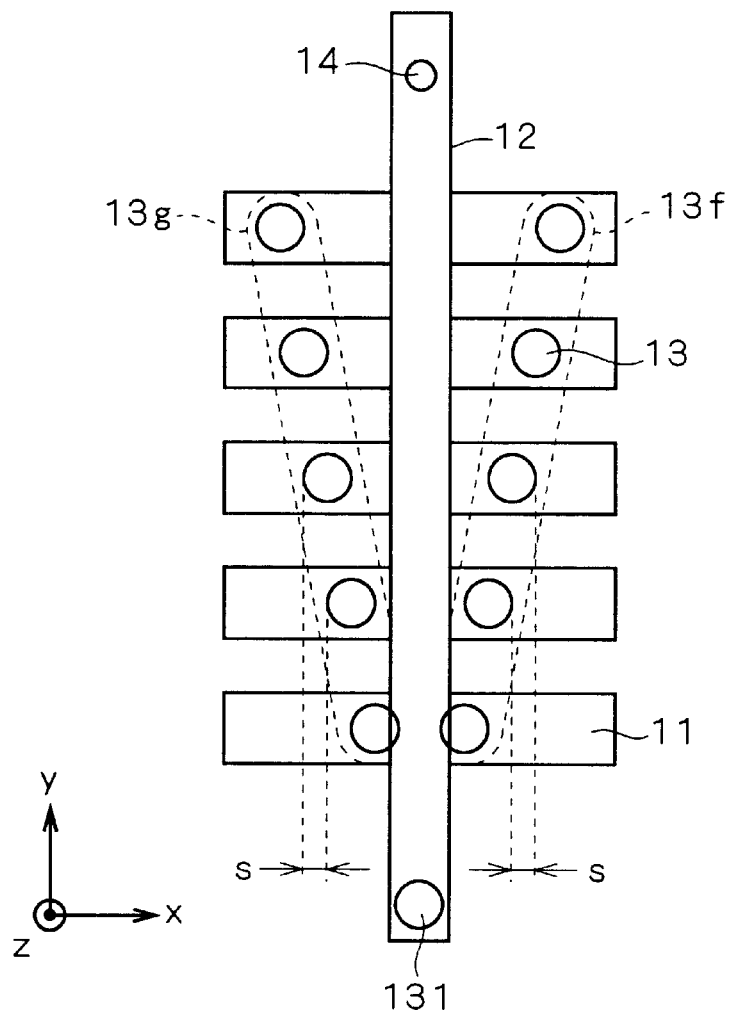
FIG. 4 shows a test pattern in the design phase according to a first preferred embodiment of the present invention.

FIG. 4 shows the designed test structure as viewed from above. In FIG. 4, the reference numeral 11 designates lower-level interconnect lines; 12 designates a first upper-level interconnect line (or a linear conductor); 13 designates via plugs electrically connected to the lower-level interconnect lines 11; and 14 designates a first potential fixing via plug for fixing the potential of the first upper-level interconnect line 12.

Used herein is a right-handed coordinate system having a y-axis extending in the longitudinal direction of the first upper-level interconnect line (or linear conductor) 12.

Referring to FIG. 4, the lower-level interconnect lines 11 are designed in the form of stripes each extending in the x direction, and the first upper-level interconnect line 12 is designed to extend in the y direction. A via plug 131 to be measured is designed to have a diameter the center of which coincides with the center of the width of the first upper-level interconnect line 12 (d'=0).

The plurality of via plugs 13 are designed to be arranged in pairs symmetric with respect to the first upper-level interconnect line 12. Each pair of via plugs 13 are designed to be electrically connected to each other through a corresponding one of the lower-level interconnect lines 11, and to be spaced apart a distance increasing in increments of 2s (where s designates a lateral shift amount) in proceeding in the y direction. Specifically, the pairs of via plugs 13 are comprised of a first group 13f of via plugs (or first conductors) arranged in a uniformly spaced relationship in a first imaginary line having a predetermined inclination (or a first inclination), and a second group 13g of via plugs (or second conductors) arranged in a uniformly spaced relationship in a second imaginary line having an inclination equal in magnitude to and different in direction from that of the first imaginary line. The via plug 131 to be measured is positioned at the intersection of the first and second imaginary lines.

The first potential fixing via plug 14 is designed to be electrically connected to the first upper-level interconnect line 12.

Figure 5:
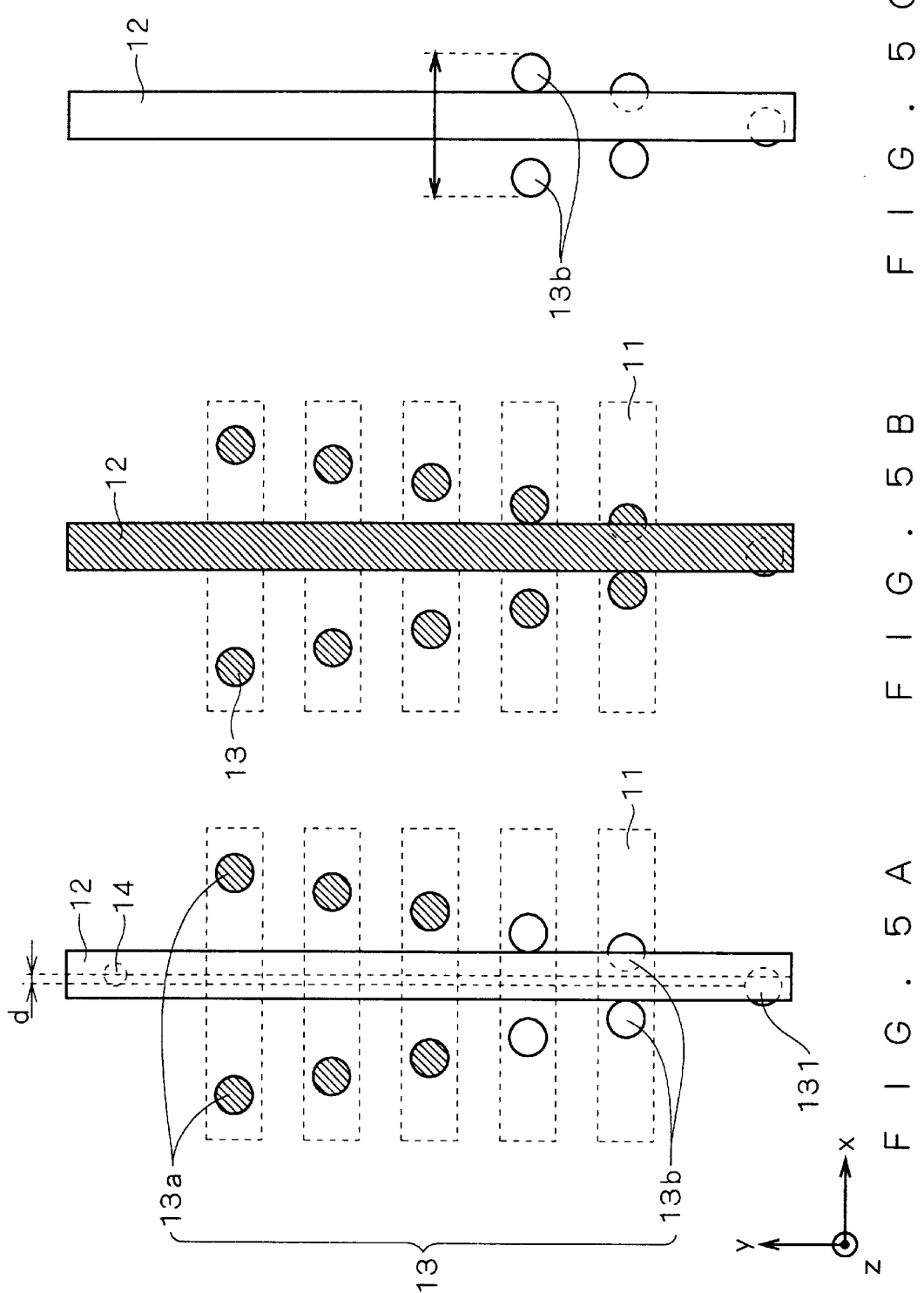
FIG. 5A shows the construction and voltage contrast of a pattern to be tested according to the first preferred embodiment.
FIG. 5B shows the construction and voltage contrast of a reference pattern according to the first preferred embodiment.
FIG. 5C shows a comparison image according to the first preferred embodiment.

A test structure is actually formed based on the design of FIG. 4, as illustrated in FIGS. 5A, 5B and 5C. The test structure of FIGS. 5A, 5B and 5C will be used for the following description.

FIG. 5A shows a pattern to be tested as viewed from above the semiconductor device 508, and the voltage contrast of this pattern. FIG. 5B shows a reference pattern for comparison with the pattern to be tested as viewed from above the semiconductor device 508, and the voltage contrast of the reference pattern. FIG. 5C shows the second comparison image produced from the first comparison image resulting from the comparison between the voltage contrast of the pattern to be tested shown in FIG. 5A and the voltage contrast of the reference pattern shown in FIG. 5B.

The pattern structure to be tested shown in FIG. 5A will be described specifically.

First, an interlayer insulation film (not shown) is deposited along the z-axis on a main surface of a silicon substrate (not shown). It will be apparent from FIG. 5A that the lower-level interconnect lines 11 are provided in the form of stripes each extending in the x direction. Since the lower-level interconnect lines 11 are formed in the interlayer insulation film, the configuration of the lower-level interconnect lines 11 is shown by dotted lines.

The plurality of via plugs 13 are formed to reach the lower-level interconnect lines 11 through the surface of the interlayer insulation film (along the z-axis). The via plugs 13 are arranged in pairs so that each pair of via plugs 13 arranged in the x direction are provided for a corresponding one of the lower-level interconnect lines 11 and are spaced apart a distance increasing in increments of 2$s$ in proceeding in the y direction.

The first upper-level interconnect line 12 extending in the y direction is formed on the surface of the interlayer insulation film. In the design phase, the via plug 131 to be measured is designed at the intersection of the first and second imaginary lines so that the center of the diameter of the via plug 131 coincides with the central axis of the first upper-level interconnect line 12 (d'=0). In the test structure actually formed, although the first and second imaginary lines have the same inclinations as those in the design phase, the center of the diameter of the via plug 131 to be measured which is positioned at the intersection of the first and second imaginary lines is deviated by the amount d in the x direction from the central axis of the first upper-level interconnect line 12. Since d'=0 is designed, the amount d of deviation of the center of the diameter of the via plug 131 from the central axis of the first upper-level interconnect line 12 corresponds to the misalignment amount d.

The first potential fixing via plug 14 extends along the z-axis to establish electrical connection between the first upper-level interconnect line 12 and the silicon substrate connected to the ground. Thus, the first upper-level interconnect line 12 is connected to the ground, and the potential of the first upper-level interconnect line 12 is fixed at the ground potential. Since the first potential fixing via plug 14 underlies the first upper-level interconnect line 12, the configuration of the first potential fixing via plug 14 is shown by the dotted line.

In the above-mentioned structure, some of the via plugs 13 formed on the lower-level interconnect lines 11 are shorted to the first upper-level interconnect line 12.

The voltage contrast of the pattern to be tested shown in FIG. 5A is described more specifically.

Observation of the pattern to be tested shown in FIG. 5A using the SEM image comparison type testing apparatus 500 of FIG. 1 (Step ST12) shows the following result. Regions whose potential is not fixed (i.e., pairs of via plugs 13$a$ which are not electrically connected to the first upper-level interconnect line 12) are electrically floating, and hence are positively charged when irradiated with the primary electron beam 502. This reduces the efficiency of generation of the secondary electrons 512 from the pairs of via plugs 13$a$. Therefore, these regions are recognized as a dark contrast image.

On the other hand, regions whose potential is fixed at the ground potential (i.e., the first upper-level interconnect line 12, and pairs of via plugs 13$b$ electrically connected to the first upper-level interconnect line 12) are not charged. Thus, these regions normally generate the secondary electrons 512 when irradiated with the primary electron beam 502. Therefore, the first upper-level interconnect line 12 and the pairs of via plugs 13$b$ are recognized as a bright contrast image.

The voltage contrast, which is produced based on only information about the potential of the topmost surface of the semiconductor device 508, reflects only information about the potentials of the first upper-level interconnect line 12 and the via plugs 13, and does not reflect information about the potentials of the lower-level interconnect lines 11 and the first potential fixing via plug 14.

The reference pattern structure shown in FIG. 5B is substantially similar to the structure shown in FIG. 5A except that the first potential fixing via plug 14 is not provided.

Observation of the reference pattern shown in FIG. 5B using the SEM image comparison type testing apparatus 500 of FIG. 1 (Step ST13) shows the following result. Regions whose potential is not fixed (i.e., the first upper-level interconnect line 12 and the via plugs 13) are electrically floating, and hence are positively charged when irradiated with the primary electron beam 502. This reduces the efficiency of generation of the secondary electrons 512 from the first upper-level interconnect line 12 and the via plugs 13. Therefore, these regions are recognized as a dark contrast image.

The voltage contrast, which is produced based on only information about the potential of the topmost surface of the semiconductor device 508, reflects only information about the potentials of the first upper-level interconnect line 12 and the via plugs 13, and does not reflect information about the potential of the lower-level interconnect lines 11.

The image comparing section 515 makes a comparison between the voltage contrasts of FIGS. 5A and 5B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 5C.

Thus, in the second comparison image shown in FIG. 5C, the first upper-level interconnect line 12 and the pairs of via plugs 13$b$ are left intact as the bright contrast regions, whereas the pair of via plugs 13$a$ are cancelled.

Next, the contrast dimension measuring section 516 effects the clustering function to recognize a minimum distance (or dimension), in the x direction, within which are contained all contrast regions corresponding to the via plugs among the contrast regions in the second comparison image of FIG. 5C, and then measures the distance (or dimension) in the x direction (Step ST15).

Thereafter, the characterizing dimension analyzing section 517 derives the actual via covering amount a of the first upper-level interconnect line 12 with respect to the via plug 131 to be measured, based on the dimension measurement obtained by the contrast dimension measuring section 516 (Step ST16). A specific analysis method will be described below.

Figure 6:
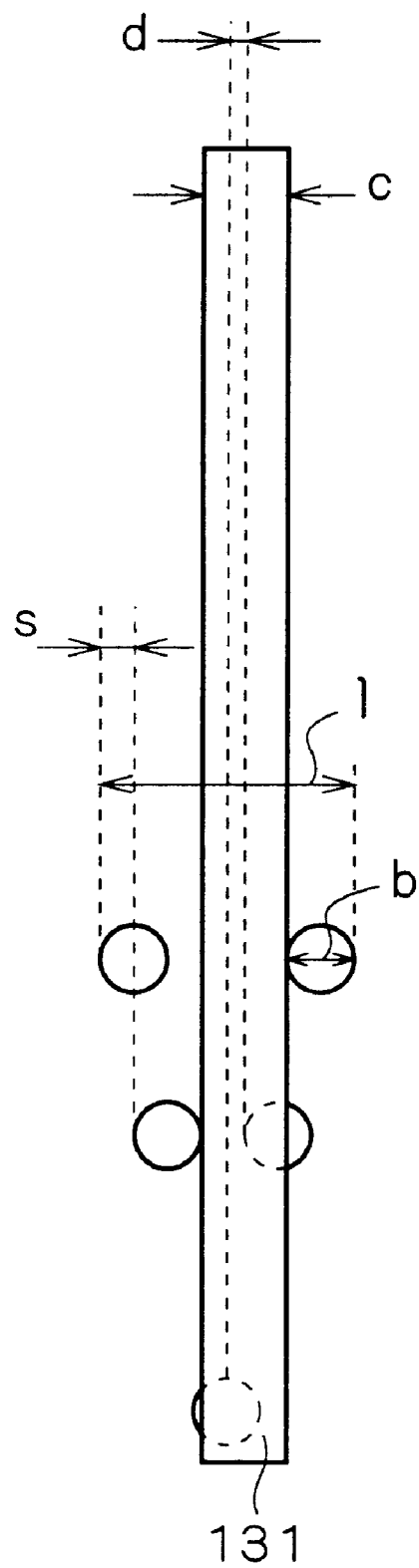
FIG. 6 is a view for determining a characterizing dimension according to the first preferred embodiment.

FIG. 6 is a view for illustrating how to derive the via covering amount a.

The minimum distance 1, in the x direction, within which all contrast regions corresponding to the via plugs shown in FIG. 6 are contained is given by $$1 = c + 2b + 2d \qquad (4)$$

where c is the width of the first upper-level interconnect line 12, and b is the diameter of the via plugs 13. The first preferred embodiment designs the lateral shift amount s to be small, thereby to make approximation such that one of the pair of via plugs 13 subjected to the measurement of the distance I when deriving Equation (4) is formed in contact with the first upper-level interconnect line 12. This approximation is regarded as appropriate when the specific value of the lateral shift amount s is approximately less than one-tenth the diameter b of the via plugs.

Substituting values separately measured by SEM for the via plug diameter b and the first upper-level interconnect line width c, and a value measured by the contrast dimension measuring section 516 for the distance 1 in Equation (4) determines the misalignment amount d.

Thus, the via covering amount a is derived from Equation (2). The characterizing dimension analyzing section 517 may previously store a correspondence table containing the dimension based on the contrast regions from Equation (4), the via covering amount a and the misalignment amount d in the form of a database, thereby to automatically and rapidly derive the characterizing dimension.

As described above, the misalignment amount d and the via covering amount a are determined by measuring the minimum distance, in the x direction, within which all contrast regions corresponding to the via plugs in the second comparison image are contained. Thus, the smaller the lateral shift amount s is designed, the higher the accuracy of the via covering amount a and the misalignment amount d is.

The first comparison image is produced from the voltage contrast of the pattern to be tested and the voltage contrast of the reference pattern, and is binarized. This facilitates measurement of the dimension based on the contrast regions, to allow automatic testing depending on settings, thereby preventing human error.

Although d'=0 is contemplated in the first preferred embodiment, the amount d' may have a finite value. This value, which is a design value and is known, is required only to be substituted into Equation (2).

As stated hereinabove, the first preferred embodiment can measure the via covering amount a and the like with high accuracy without employing the overlay measurement apparatus using an optical technique, to achieve an accurate test for poor connection of the first upper-level interconnect line to the via plug.

<Second Preferred Embodiment>

A second preferred embodiment of the present invention is also intended to determine the via covering amount a of the upper-level interconnect line 4 with respect to the via plug 3 actually formed in the semiconductor device 508, based on d'=0 (indicating that the center of the diameter of the via plug 3 coincides with the center of the width of the upper-level interconnect line 4) designed in the design phase, as shown in FIG. 3. For this purpose, a test structure shown in FIG. 7 is designed.

Figure 7:
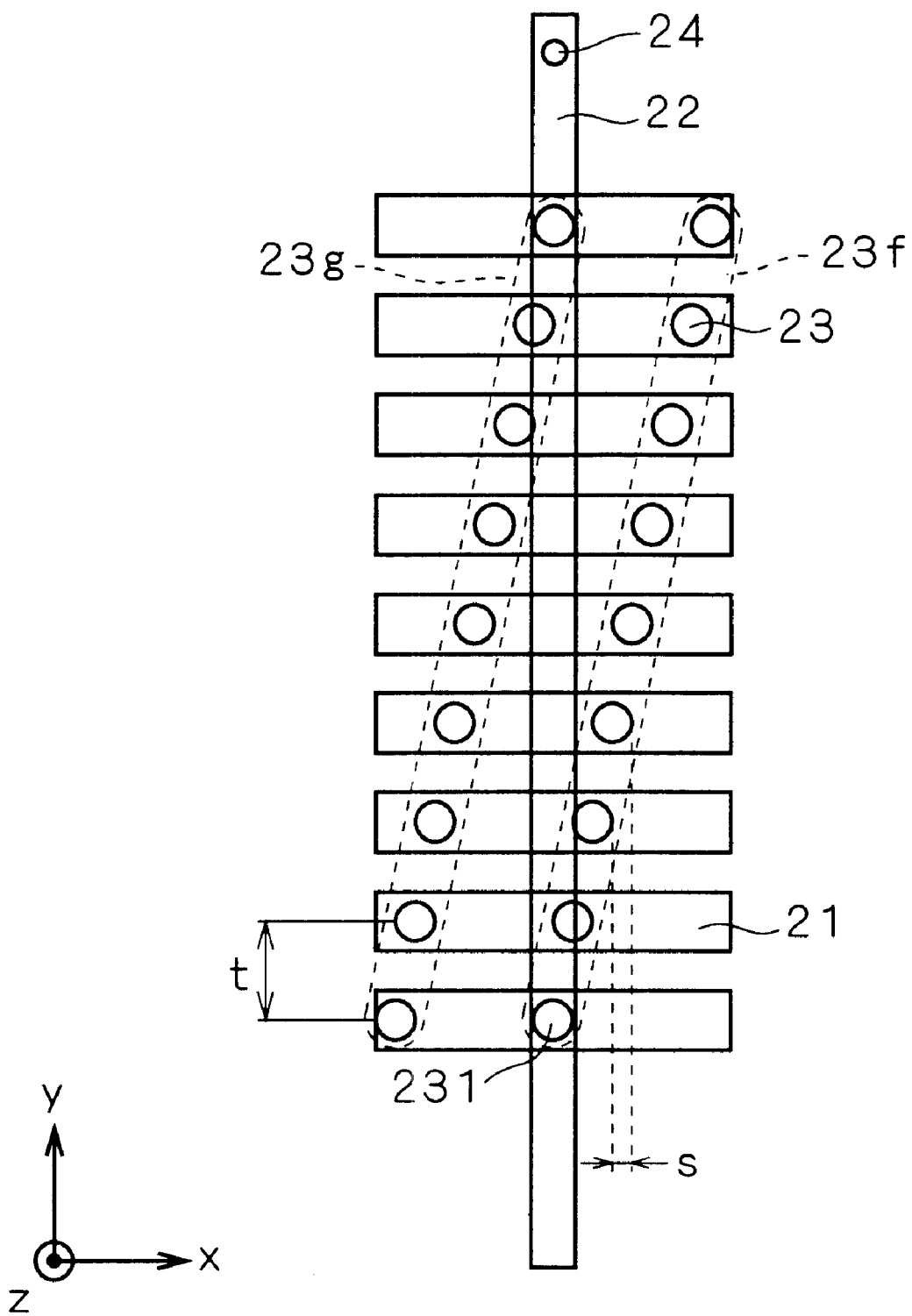
FIG. 7 shows a test pattern in the design phase according to a second preferred embodiment of the present invention.

FIG. 7 shows the designed test structure as viewed from above. In FIG. 7, the reference numeral 21 designates lower-level interconnect lines; 22 designates a first upper-level interconnect line (or a linear conductor); 23 designates via plugs electrically connected to the lower-level interconnect lines 21; and 24 designates a first potential fixing via plug for fixing the potential of the first upper-level interconnect line 22.

Referring to FIG. 7, the first upper-level interconnect line 22 is designed to extend in the y direction. The width of the first upper-level interconnect line 22 is designed to be twice as great as an upper-level interconnect line width desired to be actually evaluated. This design of the first upper-level interconnect line 22 used herein is prepared for purposes of convenience for later analysis in the characterizing dimension analyzing section 517, and does not influence the value of the via covering amount a to be calculated later.

The plurality of via plugs 23 are designed in a manner to be described below.

The via plugs 23 are comprised of a first group 23$f$ of via plugs (or first conductors), and a second group 23$g$ of via plugs (or second conductors). The via plugs in the first group 23$f$ include a via plug 231 to be measured (which is designed to have a diameter the center of which coincides with the central axis of the width of the first upper-level interconnect line 22 ( d'=0)), and are designed to be shifted by the small distance s (lateral shift amount) in the x direction at each spacing t (or a longitudinal shift mount) in the y direction.

The via plugs in the second group 23$g$ are also designed to be shifted by the small distance s (lateral shift amount) in the x direction at each spacing t (or the longitudinal shift amount) in the y direction.

Specifically, the first group 23$f$ of via plugs are arranged in a uniformly spaced relationship in a first imaginary line having a predetermined inclination (or a first inclination=t/s), and the second group 23$g$ of via plugs are arranged in a uniformly spaced relationship in a second imaginary line having the same inclination (t/s). The second group 23$g$ is designed to be spaced a predetermined distance in the −x direction apart from the first group 23$f$.

The lower-level interconnect lines 21 are designed in the form of stripes each extending in the x direction so as to establish electrical connection between the via plugs in the first group 23$f$ and the via plugs in the second group 23$g$. That is, a pair of via plugs are designed for each of the lower-level interconnect lines.

The first potential fixing via plug 24 is designed to be electrically connected to the first upper-level interconnect line 22.

A test structure is actually formed based on the design of FIG. 7, as illustrated in FIGS. 8A, 8B and 8C. The test structure of FIGS. 8A, 8B and 8C will be used for the following description.

FIG. 8A shows a pattern to be tested as viewed from above the semiconductor device 508, and the voltage contrast of this pattern. FIG. 8B shows a reference pattern for comparison with the pattern to be tested as viewed from above the semiconductor device 508, and the voltage contrast of the reference pattern. FIG. 8C shows the second comparison image produced from the first comparison image resulting from the comparison between the voltage contrast of the pattern to be tested shown in FIG. 8A and the voltage contrast of the reference pattern shown in FIG. 8B.

The pattern structure to be tested shown in FIG. 8A will be described specifically.

First, an interlayer insulation film (not shown) is deposited along the z-axis on a main surface of a silicon substrate (not shown). The lower-level interconnect lines 21 in the form of stripes each extending in the x direction are formed in the interlayer insulation film. Since the lower-level interconnect lines 21 are formed in the interlayer insulation film, the configuration of the lower-level interconnect lines 21 is shown by dotted lines.

The plurality of via plugs 23 are formed to reach the lower-level interconnect lines 21 through the surface of the interlayer insulation film (along the z-axis). The via plugs 23 are comprised of the first group 23$f$ of via plugs and the second group 23$g$ of via plugs which are arranged in the relationship described with reference to FIG. 7.

The first upper-level interconnect line 22 extending in the y direction is formed on the surface of the interlayer insulation film. In the second preferred embodiment, the test structure shown in FIGS. 8A, 8B and 8C are formed as designed in FIG. 7 without any misalignment (d=0) in the manufacture. In other words, the center of the diameter of the via plug 231 to be measured coincides with the central axis of the width of the first upper-level interconnect line 22 in the test structure shown in FIGS. 8A, 8B and 8C.

The first potential fixing via plug 24 extends along the z-axis to establish electrical connection between the first upper-level interconnect line 22 and the silicon substrate connected to the ground. Thus, the first upper-level interconnect line 22 is connected to the ground, and the potential of the first upper-level interconnect line 22 is fixed at the ground potential. Since the first potential fixing via plug 24 underlies the first upper-level interconnect line 22, the configuration of the first potential fixing via plug 24 is shown by the dotted line.

In the above-mentioned structure, some of the via plugs 23 formed on the lower-level interconnect lines 21 are shorted to the first upper-level interconnect line 22.

The voltage contrast of the pattern to be tested shown in FIG. 8A is described ore specifically.

Observation of the pattern to be tested shown in FIG. 8A using the SEM image comparison type testing apparatus 500 of FIG. 1 (Step ST12) shows the following result. Regions whose potential is not fixed (i.e., pairs of via plugs 23a which are not electrically connected to the first upper-level interconnect line 22) are electrically floating, and hence are positively charged when irradiated with the primary electron beam 502. This reduces the efficiency of generation of the secondary electrons 512 from the pairs of via plugs 23a. Therefore, these regions are recognized as a dark contrast image.

On the other hand, regions whose potential is fixed at the ground potential (i.e., the first upper-level interconnect line 22, and pairs of via plugs 23b electrically connected to the first upper-level interconnect line 22) are not charged. Thus, these regions normally generate the secondary electrons 512 when irradiated with the primary electron beam 502. Therefore, the first upper-level interconnect line 22 and the pairs of via plugs 23b are recognized as a bright contrast image.

The voltage contrast, which is produced based on only information about the potential of the topmost surface of the semiconductor device 508, reflects only information about the potentials of the first upper-level interconnect line 22 and the via plugs 23, and does not reflect information about the potentials of the lower-level interconnect lines 21 and the first potential fixing via plug 24.

The reference pattern structure shown in FIG. 8B is substantially similar to the structure shown in FIG. 8A but has a difference therefrom to be described below.

The difference is that the reference pattern structure of FIG. 8B has second potential fixing via plugs 25 for fixing the potential of the lower-level interconnect lines 21.

The second potential fixing via plugs 25 extend along the z-axis to establish electrical connection between the lower-level interconnect lines 21 and the silicon substrate connected to the ground. Thus, the lower-level interconnect lines 21 are connected to the ground, and the potential of the lower-level interconnect lines 21 is fixed at the ground potential. Since the second potential fixing via plugs 25 underlie the lower-level interconnect lines 21, the configuration of the second potential fixing via plugs 25 is shown by the dotted lines.

Observation of the reference pattern shown in FIG. 8B using the SEM image comparison type testing apparatus 500 of FIG. 1 (Step ST13) shows the following result. Regions whose potential is fixed at the ground potential (i.e., the first upper-level interconnect line 22, and the via plugs 23) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The image comparing section 515 makes a comparison between the voltage contrasts of FIGS. 8A and 8B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 8C.

Thus, in the second comparison image shown in FIG. 8C, the pairs of via plugs 23a are left intact as the dark contrast regions, whereas the pairs of via plugs 23b and the first upper-level interconnect line 22 are cancelled.

Next, the contrast dimension measuring section 516 effects the clustering function to recognize the spaced contrast regions in the second comparison image of FIG. 8C as a cluster, and measures the dimensions of the cluster (Step ST15). The cluster used herein is defined to have the shape of a rectangle having a minimum size required to contain all contrast regions, and the contrast dimension measuring section 516 measures the dimensions of the rectangle in the x and y directions.

Thereafter, the characterizing dimension analyzing section 517 derives the actual via covering amount a of the upper-level interconnect line 4 with respect to the via plug 3 depicted in FIG. 3, based on the dimension measurements obtained by the contrast dimension measuring section 516 (Step ST16). A specific analysis method will be described below.

The dimension Y of the cluster in the y direction is given by $$Y = b + (n-1) \cdot t \quad (5)$$

where b is the diameter of the via plugs 23, t is the longitudinal shift amount, and n is the number of pairs of contrast regions corresponding to the via plugs recognized.

Substituting the dimension measurement of the cluster in the y direction obtained by the contrast dimension measuring section 516 into Equation (5) and assuming that t>>b (which condition is easily achievable from the design point of view) determine the value of n.

$$n = Y/t + 1 \quad (6)$$

The characterizing dimension analyzing section 517 can recognize the value of n from Equation (6). Although the value of n is calculated from Equation (6) in the form of a decimal fraction, the characterizing dimension analyzing section 517 recognizes an integer nearest to the value of n.

The dimension X of the cluster in the x direction is given by $$X = 2c + 2b + 2n \cdot s \quad (7)$$

where 2c is the width of the first upper-level interconnect line, and s is the lateral shift amount. Equation (7) is derived using the lateral shift amount s which is small. In other words, at least one of the via plugs 23 lined up to cross the first upper-level interconnect line 22 is approximately in contact with the first upper-level interconnect line 22. This approximation is regarded as appropriate when the specific value of the lateral shift amount s is approximately less than one-tenth the diameter b of the via plugs.

From Equation (7), $$b + c = X/2 - n \cdot s \quad (8)$$

Substituting Equation (8) into Equation (2) derives $$a = (X - 2n \cdot s)/4 \quad (9)$$

The condition d=d'=0 contemplated in the second preferred embodiment is taken into consideration herein.

Substituting the dimension measurement X of the cluster in the x direction obtained by the contrast dimension measuring section 516 and the integer n approximated by Equation (6) into Equation (9) determines the value of the via covering amount a in the characterizing dimension analyzing section 517.

The characterizing dimension analyzing section 517 may previously store a correspondence table containing the dimensions X and Y of the cluster (or the integer n) based on Equation (9) and the via covering amount a in the form of a database, thereby to automatically and rapidly derive the characterizing dimension.

As described above, the via covering amount a is determined by measuring the dimensions of the cluster of contrast regions in the second comparison image containing only one of two binary contrast levels (bright or dark) resulting from the binarization. Thus, the greater the longitudinal shift amount t is designed or the smaller the lateral shift amount s is designed, the higher the accuracy of the via covering amount a is. This allows an accurate test for connection of the upper-level interconnect line to the via plug.

The first preferred embodiment, in which the second comparison image includes the contrast image of the first upper-level interconnect line, requires difficult processing to select only desired contrast regions by the use of the clustering function. However, the second preferred embodiment can easily establish the cluster using the clustering function since only the contrast regions required to determine the characteristic dimension appear in the second comparison image of FIG. 8C.

Additionally, the second preferred embodiment handles the images in digital form to allow automation of the above-mentioned series of processing by simple setting.

Although d'=0 is contemplated in the second preferred embodiment, the amount d' may have a finite value. This value, which is a design value and is known, is required only to be substituted into Equation (2).

<Third Preferred Embodiment>

A third preferred embodiment of the present invention is a modification of the second preferred embodiment. In the second preferred embodiment, the via covering amount a is determined when the test structure is formed without misalignment. On the other hand, the third preferred embodiment is intended to measure the via covering amount a of the upper-level interconnect line with respect to the via plug formed in the semiconductor device 508 and the misalignment amount d of the upper-level interconnect line with respect to the via plug when the misalignment amount d is not equal to zero.

A test structure (FIGS. 10A, 10B and 10C) is actually formed based on the design of FIG. 9. The design of FIG. 9 (in the third preferred embodiment) is substantially similar to the design of FIG. 7 (in the second preferred embodiment) but has difference to be described below.

The difference lies in selecting a lower-level interconnect line 31c serving as a reference site for establishing electrical connection between a pair of via plugs 33c symmetrical with respect to a first upper-level interconnect line 32 and in designing a second potential fixing via plug 35 for fixing the potential of the lower-level interconnect line 31c in the lower-level interconnect line 31c.

The test structure of FIGS. 10A, 10B and 10C will be used for the following description.

FIG. 10A shows a pattern to be tested as viewed from above the semiconductor device 508, and the voltage contrast of this pattern. FIG. 10B shows a reference pattern for comparison with the pattern to be tested as viewed from above the semiconductor device 508, and the voltage contrast of the reference pattern. FIG. 10C shows the second comparison image produced from the first comparison image resulting from the comparison between the voltage contrast of the pattern to be tested shown in FIG. 10A and the voltage contrast of the reference pattern shown in FIG. 10B.

In FIGS. 10A and 10B, the reference numeral 31 designates lower-level interconnect lines; 32 designates the first upper-level interconnect line (or a linear conductor); 33 designates via plugs electrically connected to the lower-level interconnect lines 31; 34 designates a first potential fixing via plug for fixing the potential of the first upper-level interconnect line 32; and 35 designates second potential fixing via plugs for fixing the potential of the lower-level interconnect lines 31.

The pattern structure to be tested shown in FIG. 10A is substantially similar to the pattern structure to be tested shown in FIG. 8A but has differences to be described below.

The first difference is that the second potential fixing via plug 35 extends along the z-axis to establish electrical connection between the lower-level interconnect line 31c serving as the reference site and the silicon substrate connected to the ground. Thus, the lower-level interconnect line 31c serving as the reference site is connected to the ground, and the potential of the lower-level interconnect line 31c is fixed at the ground potential. Since the second potential fixing via plug 35 underlies the lower-level interconnect line 31c, the configuration of the second potential fixing via plug 35 is shown by the dotted line.

The second difference is that the central axis of the width of the first upper-level interconnect line 32 is deviated by the amount d in the x direction from the center of the diameter of a via plug 331 to be measured when the actual test structure is formed in the third preferred embodiment.

Since d'=0 is designed, the amount d of deviation corresponds to the misalignment amount.

In the above-mentioned structure, some of the via plugs 33 formed on the lower-level interconnect lines 31 are shorted to the first upper-level interconnect line 32.

The voltage contrast of the pattern to be tested shown in FIG. 10A is described more specifically.

Observation of the pattern to be tested shown in FIG. 10A using the SEM image comparison type testing apparatus 500 of FIG. 1 (Step ST12) shows the following result. Regions whose potential is not fixed (i.e., pairs of via plugs 33a which are not electrically connected to the first upper-level interconnect line 32 except for the pair of via plug 33c) are electrically floating, and hence are positively charged when irradiated with the primary electron beam 502. This reduces the efficiency of generation of the secondary electrons 512 from the pairs of via plugs 33a. Therefore, these regions are recognized as a dark contrast image.

On the other hand, regions whose potential is fixed at the ground potential (i.e., the first upper-level interconnect line 32, pairs of via plugs 33b electrically connected to the first upper-level interconnect line 32, and the pair of via plugs 33c) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The reference pattern structure shown in FIG. 10B is substantially similar to the structure shown in FIG. 10A but has a difference therefrom to be described below.

The difference is that the second potential fixing via plugs 35 for fixing the potential of the lower-level interconnect lines 31 are provided for all of the lower-level interconnect lines 31.

The second potential fixing via plugs 35 extend along the z-axis to establish electrical connection between the lower-level interconnect lines 31 and the silicon substrate connected to the ground. Thus, the lower-level interconnect lines 31 are connected to the ground, and the potential of the lower-level interconnect lines 31 is fixed at the ground potential. Since the second potential fixing via plugs 35 underlie the lower-level interconnect lines 31, the configuration of the second potential fixing via plugs 35 is shown by the dotted lines.

Observation of the reference pattern shown in FIG. 10 B using the SEM image comparison type testing apparatus 500 of FIG. 1 (Step ST13) shows the following result. Regions whose potential is fixed at the ground potential (i.e., the first upper-level interconnect line 32, and the via plugs 33) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The image comparing section 515 makes a comparison between the voltage contrasts of FIGS. 10A and 10B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 10C.

Thus, in the second comparison image shown in FIG. 10C, the pairs of via plugs 33a are left intact as the dark contrast regions, whereas the pairs of via plugs 33b and 33c and the first upper-level interconnect line 32 are cancelled.

Next, the via covering amount a and the misalignment amount d are determined using the second comparison image shown in FIG. 10C. First, a method of determining the misalignment amount d will be described.

The contrast dimension measuring section 516 effects the clustering function to recognize the spaced contrast regions in the second comparison image of FIG. 10C as two clusters 38 and 39, and measures the dimension of the clusters 38 and 39 (Step ST15). Each of the clusters used herein is defined to have the shape of a rectangle having a minimum size required to contain corresponding contrast regions, and the contrast dimension measuring section 516 measures the dimension of each rectangle in the y direction.

Thereafter, the characterizing dimension analyzing section 517 derives the actual misalignment amount d of the first upper-level interconnect line 32 with respect to the patterned via plug 331 to be measured, based on the dimension measurements obtained by the contrast dimension measuring section 516 (Step ST16). A specific analysis method will be described below.

If the misalignment amount d equals zero, the via plugs 33 are arranged in inversion-symmetrical relation with respect to the lower-level interconnect line 31c. In this case, a dimension Y1 of the cluster 38 in the y direction equals a dimension Y2 of the cluster 39 in the y direction, and a difference between the dimensions Y1 and Y2 equals zero.

In the actual manufacture of the semiconductor device 508, a misalignment occurs to produce a difference between the dimensions Y1 and Y2. When the longitudinal shift amount t is made greater relative to the via plug diameter b and the lateral shift amount s is made small, the misalignment amount d is expressed as $$d=(n1-n2) \cdot s \tag{10}$$

where n1 and n2 are the number of pairs of contrast regions corresponding to the via plugs included in the cluster 38 and the number of pairs of contrast regions corresponding to the via plugs included in the cluster 39, respectively, and are integers (or the nearest integers if n1 and n2 are represented by decimal fractions) determined by using Equation (6) and the dimension measurements Y1 and Y2. Substituting the integers n1 and n2 into Equation (10) determines the misalignment amount d.

The specific value of the lateral shift amount s approximately less than one-tenth the via plug diameter b is regarded as sufficiently small.

As described above, the misalignment amount d is determined by measuring the dimensions Y1 and Y2 of the respective clusters 38 and 39 in the y direction in the second comparison image shown in FIG. 10C and recognizing the integers n1 and n2 from Equation (6) by the characterizing dimension analyzing section 517 in the third preferred embodiment. Thus, the greater the longitudinal shift amount t is designed and the smaller the lateral shift amount s is designed, the higher the accuracy of the misalignment amount d is.

The characterizing dimension analyzing section 517 may previously store a correspondence table containing the dimensions Y1 and Y2 of the clusters 38 and 39 (or the integers n1 and n1) based on Equation (10) and the misalignment amount d in the form of a database, thereby to automatically and rapidly derive the characterizing dimension.

The via covering amount a, which is derived by a similar analysis method to that of the second preferred embodiment, is not particularly described in the third preferred embodiment. It should be noted that the above derived misalignment amount d must be added to Equation (9) since the misalignment amount d is not equal to zero in the third preferred embodiment.

Although d'=0 is contemplated in the third preferred embodiment, the amount d' may have a finite value. This value, which is a design value and is known, is required only to be substituted into Equation (2).

<Fourth Preferred Embodiment>

A fourth preferred embodiment of the present invention is another modification of the second preferred embodiment. The contrast regions in the second comparison image of FIG. 8C obtained in the second preferred embodiment have a size corresponding to the diameter of the via plugs. This size is so small that it is difficult to recognize the contrast regions when defining the cluster of contrast regions by using the clustering function, sometimes resulting in failure to correctly define the cluster. The fourth preferred embodiment is intended to overcome such a problem. In the fourth preferred embodiment, a test structure shown in FIGS. 11A, 11B and 11C is formed.

FIG. 11A shows a pattern to be tested as viewed from above the semiconductor device 508, and the voltage contrast of this pattern. FIG. 11B shows a reference pattern for comparison with the pattern to be tested as viewed from above the semiconductor device 508, and the voltage contrast of the reference pattern. FIG. 11C shows the second comparison image produced from the first comparison image resulting from the comparison between the voltage contrast of the pattern to be tested shown in FIG. 11A and the voltage contrast of the reference pattern shown in FIG. 11B.

In FIGS. 11A and 11B, the reference numeral 41 designates lower-level interconnect lines; 42 designates a first upper-level interconnect line (or a linear conductor); 43 designates via plugs electrically connected to the lower-level interconnect lines 41; 44 designates a first potential fixing via plug for fixing the potential of the first upper-level interconnect line 42; and 45 designates second potential fixing via plugs for fixing the potential of the lower-level interconnect lines 41. The first upper-level interconnect line 42 has the width c in the fourth preferred embodiment.

It is assumed that there is no misalignment in the manufacture in the fourth preferred embodiment, as in the second preferred embodiment.

As will be found from FIGS. 11A, 11B and 11C, the test structure of the fourth preferred embodiment comprises a plurality of insular conductors 46 having an area greater than the area of the via plugs in addition to the components of the test structure shown in FIGS. 8A, 8B and 8C (in the second preferred embodiment).

The insular conductors 46 are formed in the same layer (or level) as the first upper-level interconnect line 42 so as not to be connected to the first upper-level interconnect line 42. The insular conductors 46 are disposed in an isolated manner over he individual lower-level interconnect lines 41 in corresponding relation thereto. The insular conductors 46 are electrically connected to the plurality of via plugs 43.

The voltage contrast of the pattern to be tested shown in FIG. 11A is described more specifically.

Observation of the pattern to be tested shown in FIG. 11A using the SEM image comparison type testing apparatus 500 of FIG. 1 (Step ST12) shows the following result. Regions whose potential is not fixed (i.e., pairs of via plugs 43a which are not electrically connected to the first upper-level interconnect line 42, and insular conductors 46a electrically connected to the pairs of via plugs 43a) are electrically floating, and hence are positively charged when irradiated with the primary electron beam 502. This reduces the efficiency of generation of the secondary electrons 512 from the pairs of via plugs 43a and the insular conductors 46a. Therefore, these regions are recognized as a dark contrast image.

On the other hand, regions whose potential is fixed at the ground potential (i.e., the first upper-level interconnect line 42, pairs of via plugs 43b electrically connected to the first upper-level interconnect line 42, and insular conductors 46b electrically connected to the pairs of via plugs 43b) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The reference pattern structure shown in FIG. 11B is substantially similar to the structure shown in FIG. 11A but has a difference therefrom to be described below.

The difference is that the second potential fixing via plugs 45 for fixing the potential of the lower-level interconnect lines 41 are provided for all of the lower-level interconnect lines 41 in the reference pattern structure of FIG. 11B. The second potential fixing via plugs 45 extend along the z-axis to establish electrical connection between the lower-level interconnect lines 41 and the silicon substrate connected to the ground. Thus, the lower-level interconnect lines 41 are connected to the ground, and the potential of the lower-level interconnect lines 41 is fixed at the ground potential. Since the second potential fixing via plugs 45 underlie the lower-level interconnect lines 41, the configuration of the second potential fixing via plugs 45 is shown by the dotted lines.

Observation of the reference pattern shown in FIG. 11B using the SEM image comparison type testing apparatus 500 of FIG. 1 (Step ST13) shows the following result. Regions whose potential is fixed at the ground potential (i.e., the first upper-level interconnect line 42, the via plugs 43 and the insular conductors 46) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The image comparing section 515 makes a comparison between the voltage contrasts of FIGS. 11A and 11B thus obtained (Step ST14). This comparison is made by obtaining a contrast difference therebetween. Specifically, as a result of comparison, a region which appears as a bright contrast region (or dark contrast region) in-both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 11C.

Thus, in the second comparison image shown in FIG. 11C, the pairs of via plugs 43a and the insular conductors 46a are left intact as the dark contrast regions, whereas the pairs of via plugs 43b, the insular conductors 46b and the first upper-level interconnect line 42 are cancelled.

Next, the contrast dimension measuring section 516 effects the clustering function to recognize the contrast regions in the second comparison image of FIG. 11C as herein is defined to have the shape of a rectangle having a minimum size required to contain all contrast regions, and the contrast dimension measuring section 516 measures the dimensions of the rectangle in the x and y directions.

Thereafter, the characterizing dimension analyzing section 517 derives the actual via covering amount a of the first upper-level interconnect line 42 with respect to a patterned via plug 431 to be measured, based on the dimension measurements obtained by the contrast dimension measuring section 516 (Step ST16). A specific analysis method will be described below.

In Equation (5), b is changed to p where p is the width of the insular conductors 46 in the y direction. Then, substituting the dimension of the cluster in the y direction measured by the contrast dimension measuring section 516 into Equation (5) in which p is substituted for b and assuming that t>>p (which condition is easily achievable from the design point of view) provide the value of n from Equation (6).

The characterizing dimension analyzing section 517 can recognize the value of n from Equation (6). Although the value of n is calculated from Equation (6) in the form of a decimal fraction in some cases, the characterizing dimension analyzing section 517 recognizes an integer nearest to the value of n.

From Equation (7), the dimension X of the cluster in the x direction is given by $$X = c + 2b + 2n \cdot s = u + b + (n-1) \cdot s \quad (11)$$

where u is a center-to-center distance between each pair of via plugs 43. In the fourth preferred embodiment, the first upper-level interconnect line 42 has the width c. Equation (11) is derived using the lateral shift amount s (<b/10) which is small. In other words, at least one of the via plugs 43 lined up to cross the first upper-level interconnect line 42 is approximately in contact with the first upper-level interconnect line 42.

From Equation (11), $$(b+c)/2 = u/2 - (n+1) \cdot s/2 \quad (12)$$

Substituting Equation (12) into Equation (2) derives the actual via covering amount a of the first upper-level interconnect line 42 with respect to the via plug 431 to be measured.

$$a = u/2 - (n+1) \cdot s/2 \quad (13)$$

The condition d=d'=0 contemplated in the fourth preferred embodiment is taken into consideration herein.

Substituting the integer approximated by Equation (6) for n in Equation (13) determines the value of the via covering amount a in the characterizing dimension analyzing section 517. The values u, s and t are design values and are known.

As described above, the via covering amount a is determined by measuring the dimensions of the cluster of contrast regions in the second comparison image shown in FIG. 11C. Thus, the greater the longitudinal shift amount t is designed and the smaller the lateral shift amount s is designed, the higher the accuracy of the via covering amount a is.

The fourth preferred embodiment employs the insular conductors 46 greater in area than the via plugs 43 to allow the contrast regions to be more clearly recognized, thereby achieving the establishment of the cluster of contrast regions more easily and accurately.

Although d'=0 is contemplated in the fourth preferred embodiment, the amount d' may have a finite value. This value, which is a design value and is known, is required only to be substituted into Equation (2).

The fourth preferred embodiment may have a lower-level interconnect line serving as the reference site in the pattern to be tested, as in the third preferred embodiment. This allows the calculation of the amount of misalignment, if any, in the actual pattern formation.

Also in the fourth preferred embodiment, the characterizing dimension analyzing section 517 may previously store a correspondence table containing the dimensions X and Y of the cluster (or the integer n) based on Equation (13) and the via covering amount a in the form of a database, thereby to automatically and rapidly derive the characterizing dimension.

It is needless to say that the insular conductors in the fourth preferred embodiment are applicable to other preferred embodiments.

<Fifth Preferred Embodiment>

A fifth preferred embodiment of the present invention is also intended to determine the via covering amount a and misalignment amount d of the upper-level interconnect line 4 with respect to the via plug 3 actually formed in the semiconductor device 508, based on d'=0 (indicating that the center of the diameter of the via plug 3 coincides with the center of the width of the upper-level interconnect line 4) designed in the design phase, as shown in FIG. 3. For this purpose, a test structure shown in FIG. 12 is designed.

Figure 12:
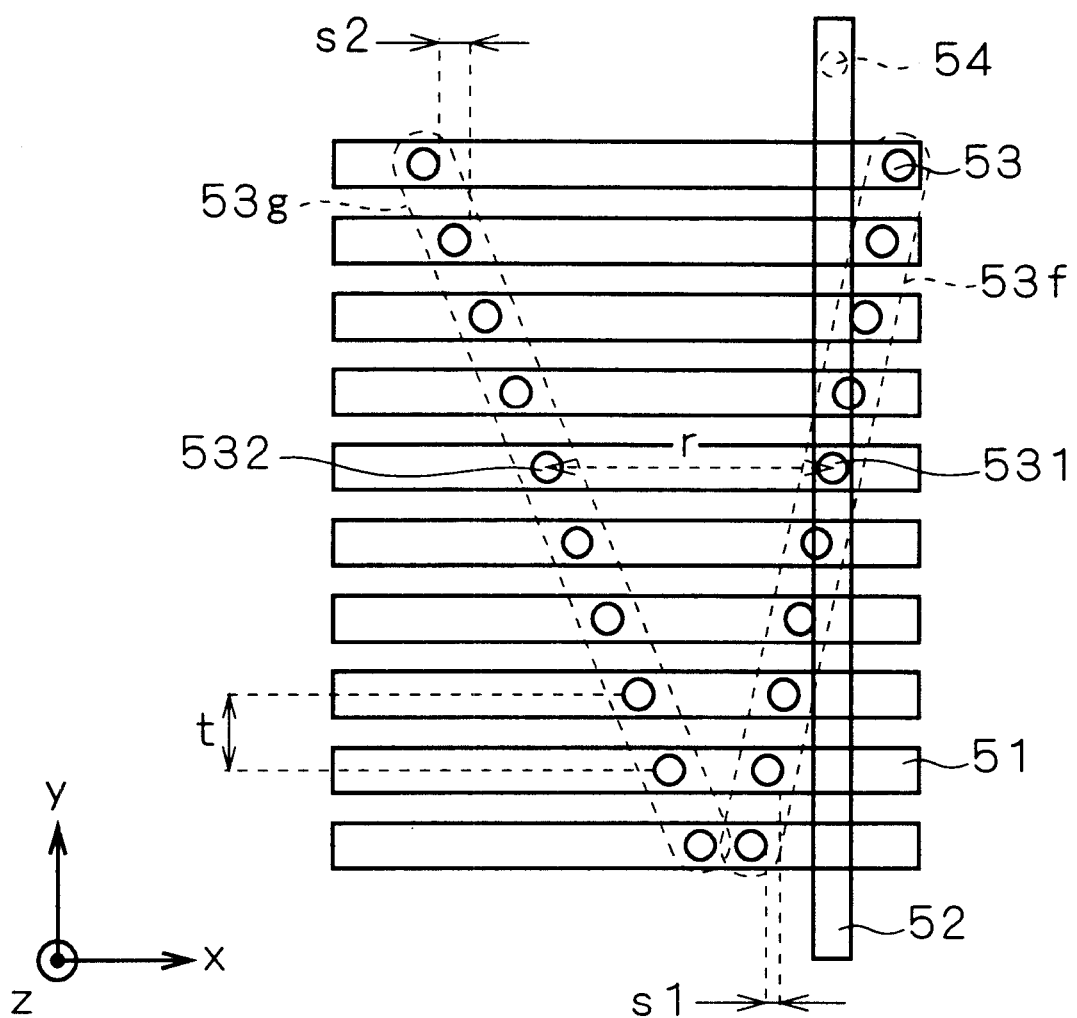
FIG. 12 shows a test pattern in the design phase according to a fifth preferred embodiment of the present invention.

FIG. 12 shows the designed test structure as viewed from above. In FIG. 12, the reference numeral 51 designates lower-level interconnect lines; 52 designates a first upper-level interconnect line (or a linear conductor); 53 designates via plugs electrically connected to the lower-level interconnect lines 51; and 54 designates a first potential fixing via plug for fixing the potential of the first upper-level interconnect line 52.

Referring to FIG. 12, the first upper-level interconnect line 52 is designed to extend in the y direction.

A via plug 531 to be measured is designed so that the center of the diameter of the via plug 531 coincides with the central axis of the width of the first upper-level interconnect line 52 ( d'=0).

A via plug 532 is designed to be spaced a distance r in the −x direction apart from the via plug 531 to be measured so that the via plugs 531 and 532 form a pair.

The plurality of via plugs 53 are comprised of a first group 53$f$ of via plugs (or first conductors) including the via plug 531, and a second group 53$g$ of via plugs (or second conductors) including the via plug 532.

The via plugs in the first group 53$f$ are arranged in a uniformly spaced relationship in a first imaginary line having a predetermined inclination (or a first inclination). The via plugs in the first group 53$f$ are designed so that each is shifted by a distance t (or the longitudinal shift amount) in the y direction and by a distance s1 (or a first lateral shift amount) in the x direction from its adjacent one. That is, the inclination of the first imaginary line is expressed as t/s1, and the spacing between the via plugs in the first group 53$f$ is expressed as $(t^2 + s1^2)^{1/2}$.

On the other hand, the via plugs in the second group 53$g$ are arranged in a uniformly spaced relationship in a second imaginary line having a predetermined inclination (or a second inclination). The via plugs in the second group 53$g$ are designed so that each is shifted by the distance t (or the longitudinal shift amount) in the y direction and by a distance s2 (or a second lateral shift amount) in the x direction from its adjacent one. That is, the inclination of the second imaginary line is expressed as t/s2, and the spacing between the via plugs in the second group 53g is expressed as $(t^2+s2^2)^{1/2}$.

Although the directions of shifting by the distances s1 and s2 may be opposite from those described above as far as the relation s2>s1 is satisfied, it is desirable that the directions of shifting by the distances s1 and s2 are opposite from each other. The via plugs in the first group 53f and the via plugs in the second group 53g form respective pairs, and two via plugs of each pair are arranged in the x direction.

The lower-level interconnect lines 51 are designed in the form of stripes each extending in the x direction to establish electrical connection between respective pairs of via plugs 53. The first potential fixing via plug 54 is designed to be connected to the first upper-level interconnect line 52.

Figure 13:
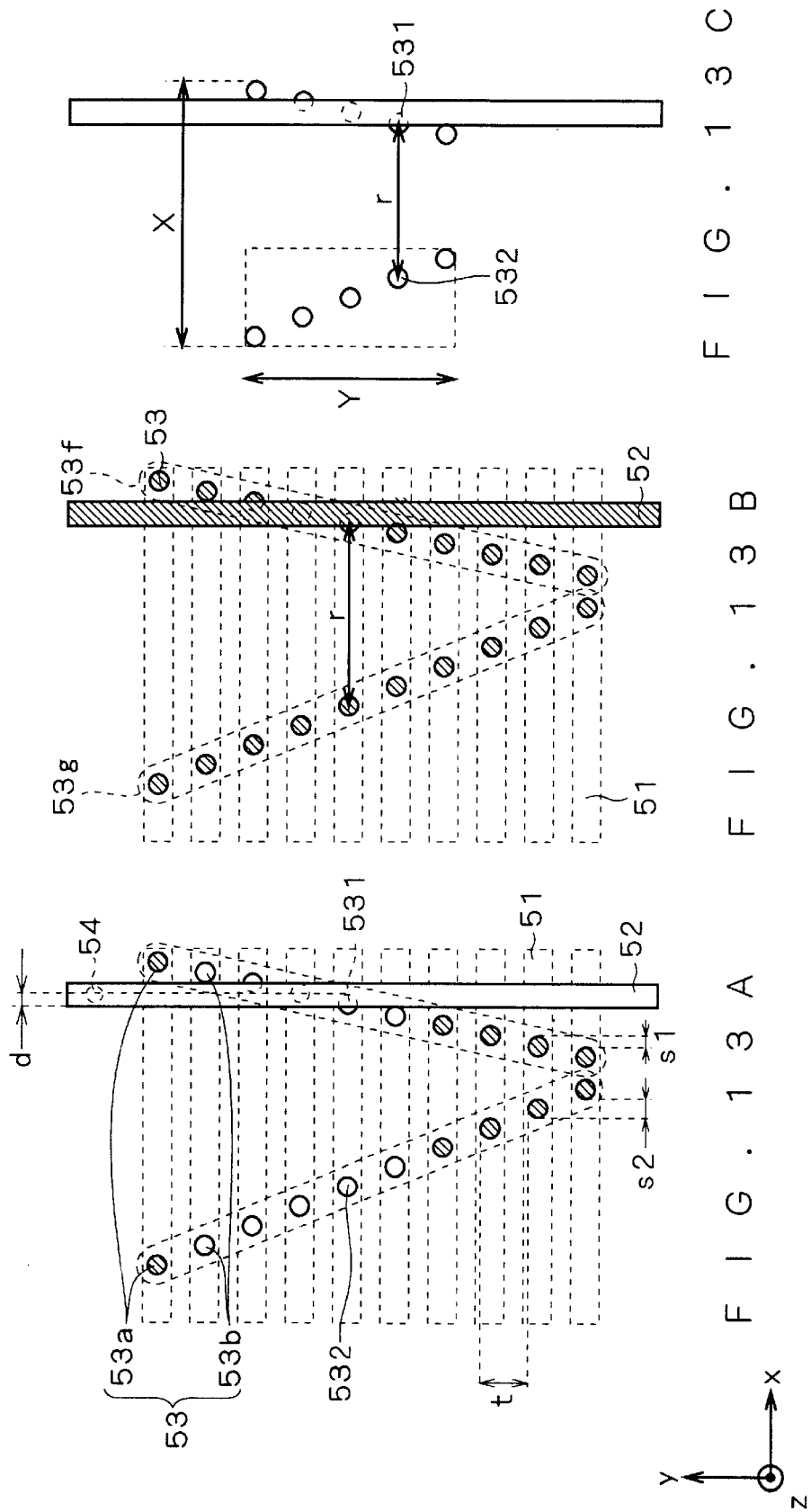
FIG. 13A shows the construction and voltage contrast of a pattern to be tested according to the fifth preferred embodiment.
FIG. 13B shows the construction and voltage contrast of a reference pattern according to the fifth preferred embodiment.
FIG. 13C shows a comparison image according to the fifth preferred embodiment.

A test structure is actually formed based on the design of FIG. 12, as illustrated in FIGS. 13A, 13B and 13C. The test structure of FIGS. 13A, 13B and 13C will be used for the following description.

FIG. 13A shows a pattern to be tested as viewed from above the semiconductor device 508, and the voltage contrast of this pattern. FIG. 13B shows a reference pattern for comparison with the pattern to be tested as viewed from above the semiconductor device 508, and the voltage contrast of the reference pattern. FIG. 13C shows the second comparison image produced from the first comparison image resulting from the comparison between the voltage contrast of the pattern to be tested shown in FIG. 13A and the voltage contrast of the reference pattern shown in FIG. 13B.

The pattern structure to be tested shown in FIG. 13A will be described specifically.

First, an interlayer insulation film (not shown) is deposited along the z-axis on a main surface of a silicon substrate (not shown). It will be apparent from FIG. 13A that the lower-level interconnect lines 51 in the form of stripes each extending in the x direction are formed in the interlayer insulation film. The lower-level interconnect lines 51 are arranged at the spacing t (the longitudinal shift amount). Since the lower-level interconnect lines 51 are formed in the interlayer insulation film, the configuration of the lower-level interconnect lines 51 is shown by dotted lines.

The plurality of via plugs 53 are formed to reach the lower-level interconnect lines 51 through the surface of the interlayer insulation film (along the z-axis). The via plugs 53 are comprised of the first group 53f of via plugs and the second group 53g of via plugs which are arranged in the relationship described with reference to FIG. 12.

The first upper-level interconnect line 52 extending in the y direction is formed on the surface of the interlayer insulation film.

In the design phase, the first upper-level interconnect line 52 is designed so that the center of the diameter of the via plug 531 to be measured coincides with the central axis of the width of the first upper-level interconnect line 52. In the test structure actually formed, however, the central axis of the width of the first upper-level interconnect line 52 is deviated by the amount d in the x direction from the center of the diameter of the via plug 531. Since d'=0 is designed, the amount d of deviation corresponds to the misalignment amount.

The first potential fixing via plug 54 extends along the z-axis to establish electrical connection between the first upper-level interconnect line 52 and the silicon substrate connected to the ground. Thus, the first upper-level interconnect line 52 is connected to the ground, and the potential of the first upper-level interconnect line 52 is fixed at the ground potential. Since the first potential fixing via plug 54 underlies the first upper-level interconnect line 52, the configuration of the first potential fixing via plug 54 is shown by the dotted line.

In the above-mentioned structure, some of the via plugs in the first group 53f are shorted to the first upper-level interconnect line 52.

The voltage contrast of the pattern to be tested shown in FIG. 13A is described more specifically.

Observation of the pattern to be tested shown in FIG. 13A using the SEM image comparison type testing apparatus 500 of FIG. 1 (Step ST12) shows the following result. Regions whose potential is not fixed (i.e., pairs of via plugs 53a which are not electrically connected to the first upper-level interconnect line 52) are electrically floating, and hence are positively charged when irradiated with the primary electron beam 502. This reduces the efficiency of generation of the secondary electrons 512 from the pairs of via plugs 53a. Therefore, these regions are recognized as a dark contrast image.

On the other hand, regions whose potential is fixed at the ground potential (i.e., the first upper-level interconnect line 52, and pairs of via plugs 53b electrically connected to the first upper-level interconnect line 52) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The reference pattern structure shown in FIG. 13B is substantially similar to the structure shown in FIG. 13A but has a difference therefrom to be described below.

The difference is that the reference pattern structure shown in FIG. 13B does not have the first potential fixing via plug 54 for fixing the first upper-level interconnect line 52 at the ground potential.

Observation of the reference pattern shown in FIG. 13B using the SEM image comparison type testing apparatus 500 of FIG. 1 (Step ST13) shows the following result. Regions whose potential is not fixed (i.e., the first upper-level interconnect line 52 and the via plugs 53) are electrically floating, and hence are positively charged when irradiated with the primary electron beam 502. This reduces the efficiency of generation of the secondary electrons 512 from the first upper-level interconnect line 52 and the via plugs 53. Therefore, these regions are recognized as a dark contrast image.

The voltage contrast is produced based on only information about the potential of the topmost surface of the semiconductor device 508.

The image comparing section 515 makes a comparison between the voltage contrasts of FIGS. 13A and 13B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 13C.

Thus, in the second comparison image shown in FIG. 13C, the first upper-level interconnect line 52 and the pairs of via plugs 53b are left intact as the bright contrast regions, whereas the pair of via plugs 53a are cancelled.

Next, the contrast dimension measuring section 516 effects the clustering function to recognize the spaced contrast regions corresponding to the second group 53g of via plugs in the second comparison image of FIG. 13C as a cluster, and measures a dimension Y of the cluster in the y direction. Further, the contrast dimension measuring section 516 uses the clustering function in the x direction to measure a distance X (referred to hereinafter as a dimension X) in the x direction between a pair of most widely spaced via plugs 53 (Step ST15).

Thereafter, the characterizing dimension analyzing section 517 derives the actual via covering amount a and misalignment amount d of the first upper-level interconnect line 52 with respect to the patterned via plug 531 to be measured, based on the dimension measurements obtained by the contrast dimension measuring section 516 (Step ST16). A specific analysis method will be described below.

First, the misalignment amount d will be determined.

The dimension X is given by $$X = r + n1 \cdot (s1+s2) + b \qquad (14)$$

where n1 is the number of pairs of contrast regions corresponding to the via plugs as appearing in the +y direction from the via plug 531 to be measured, r is a distance between the center of the via plug 531 and the center of the via plug 532, s1 and s2 are the first and second lateral shift amounts, and b is the diameter of the via plugs 53.

Assuming that s1+s2>>b (which condition is easily achievable from the design point of view) in Equation (14) determines the value of n1.

$$n1 = (X-r)/(s1+s2) \qquad (15)$$

Next, the dimension Y of the cluster in the y direction is given by $$Y = b + (n1+n2) \cdot t \qquad (16)$$

where n2 is the number of pairs of contrast regions corresponding to the via plugs as appearing in the -y direction from the via plug 531 to be measured, and t is the longitudinal shift amount. In Equation (16), the value of n1 given by Equation (15) is used.

Assuming that t>>b (which condition is easily achievable from the design point of view) in Equation (16) determines the value of n2.

$$n2 = Y/t - (X-r)/(s1+s2) \qquad (17)$$

Substituting the measurements of the dimensions X and Y obtained by the contrast dimension measuring section 516 into Equations (15) and (17) determines the values of n1 and n2 which in turn are recognized by the characterizing dimension analyzing section 517. If the values of n1 and n2 are in the form of a decimal fraction, the characterizing dimension analyzing section 517 adopts the nearest integers as n1 and n2.

By the use of the integers n1 and n2 and the first lateral shift amount s1, the misalignment amount d is given by $$d = (n1-n2) \cdot s1 \qquad (18)$$

where s1 (<b/10) which is small is used.

Thus, the use of the integers n1 and n2 determined from Equations (15) and (17) determines the misalignment amount d from Equation (18).

On the other hand, the via covering amount a will be determined in a manner to be described below.

Assuming that the first lateral shift amount s1, is small (i.e., at least one of the via plugs 53 lined up to cross the first upper-level interconnect line 52 is approximately in contact with the first upper-level interconnect line 52), the expression b+c is given by $$b+c = (n1+n2) \cdot s1 \qquad (19)$$

where c is the width of the first upper-level interconnect line 52. Thus, substituting Equations (18) and (19) into Equation (2) determines the via covering amount a.

$$a = (n1+n2) \cdot s1/2 \pm (n1-n2) \cdot s1 \qquad (20)$$

The condition d'=0 contemplated in the fifth preferred embodiment is taken into consideration herein. Therefore, substituting the integers n1 and n2 obtained from Equations (15) and (17) into Equation (20) determines the via covering amount a.

The characterizing dimension analyzing section 517 may previously store a correspondence table containing the dimensions X and Y based on the contrast regions (or the integers n1 and n2) from Equations (18) and (20), the via covering amount a and the misalignment amount d in the form of a database, thereby to automatically and rapidly derive the characterizing dimension.

As described above, the via covering amount a and the misalignment amount d are determined by measuring the dimensions based on the contrast regions in the second comparison image shown in FIG. 13C. Thus, the greater the longitudinal shift amount t and the second lateral shift amount s2 are designed or the smaller the first lateral shift amount s1, is designed, the higher the accuracy of the via covering amount a and the misalignment amount d is.

Additionally, the fifth preferred embodiment employs the second lateral shift amount s2 which is made greater than the first lateral shift amount s1 to expands the range of the dimension X. This allows the clustering function to more clearly define the range of the contrast regions in the x direction, thereby to facilitate the establishment of the range of the contrast regions in the x direction.

Although d'=0 is contemplated in the fifth preferred embodiment, the amount d' may have a finite value. This value, which is a design value and is known, is required only to be substituted into Equation (2).

<Sixth Preferred Embodiment>

A sixth preferred embodiment of the present invention is a modification of the fifth preferred embodiment. The fifth preferred embodiment can easily establish the range of the contrast regions in the x direction. The sixth preferred embodiment is intended to easily establish the range of the cluster of contrast regions also in the y direction.

The sixth preferred embodiment of the present invention is also intended to determine the via covering amount a and misalignment amount d of the upper-level interconnect line 4 with respect to the via plug 3 actually formed in the semiconductor device 508, based on d'=0 (indicating that the center of the diameter of the via plug 3 coincides with the center of the width of the upper-level interconnect line 4) designed in the design phase, as shown in FIG. 3. For this purpose, a test structure shown in FIG. 14 is designed.

Figure 14:
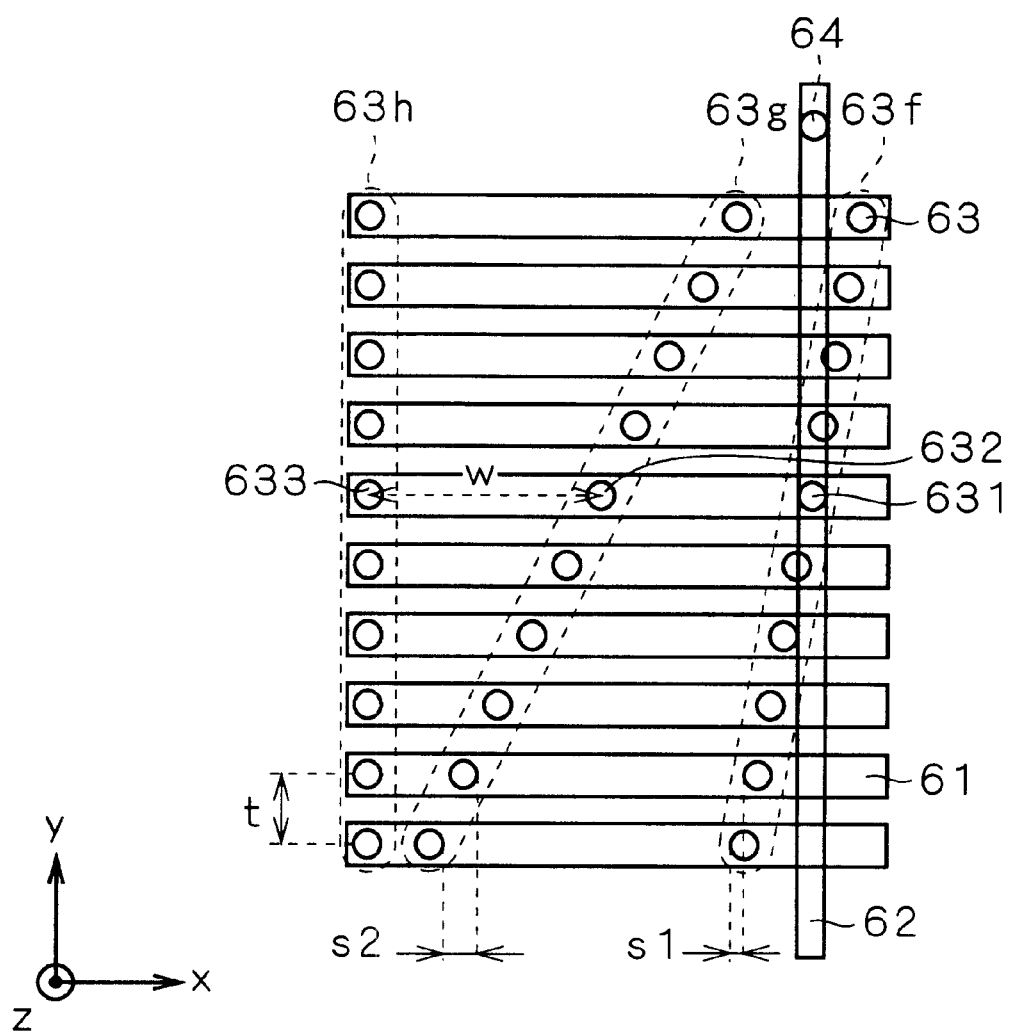
FIG. 14 shows a test pattern in the design phase according to a sixth preferred embodiment of the present invention.

FIG. 14 shows the designed test structure as viewed from above. In FIG. 14, the reference numeral 61 designates lower-level interconnect lines; 62 designates a first upper-level interconnect line (or a linear conductor); 63 designates via plugs electrically connected to the lower-level interconnect lines 61; and 64 designates a first potential fixing via plug for fixing the potential of the first upper-level interconnect line 62.

Referring to FIG. 14, the first upper-level interconnect line 62 is designed to extend in the y direction.

A via plug 631 to be measured is designed so that the center of the diameter of the via plug 631 coincides with the central axis of the width of the first upper-level interconnect line 62 ( d'=0).

A via plug 632 is designed to be spaced a predetermined distance in the −x direction apart from the via plug 631 to be measured, and a via plug 633 is designed to be spaced a distance w in the −x direction apart from the via plug 632. That is, w designates the center-to-center distance between the via plugs 632 and 633.

The plurality of via plugs 63 are comprised of a first group 63f of via plugs (or first conductors) including the via plug 631, a second group 63g of via plugs (or second conductors) including the via plug 632, and a third group 63h of via plugs including the via plug 633.

The via plugs in the first group 63f are arranged in a uniformly spaced relationship in a first imaginary line having a predetermined inclination (or a first inclination). The via plugs in the first group 63f are designed so that each is shifted by the distance t (or the longitudinal shift amount) in the y direction and by the distance s1, (or the first lateral shift amount) in the x direction from its adjacent one. That is, the inclination of the first imaginary line is expressed as t/s1, and the spacing between the via plugs in the first group 63f is expressed as $(t^2+s1^2)^{1/2}$.

On the other hand, the via plugs in the second group 63g are arranged in a uniformly spaced relationship in a second imaginary line having a predetermined inclination (or a second inclination). The via plugs in the second group 63g are designed so that each is shifted by the distance t (or the longitudinal shift amount) in the y direction and by the distance s2 (or the second lateral shift amount) in the x direction from its adjacent one. That is, the inclination of the second imaginary line is expressed as t/s2, and the spacing between the via plugs in the second group 63g is expressed as $(t^2+s2^2)^{1/2}$.

Further, the via plugs in the third group 63h are arranged at the spacing t (or the longitudinal shift amount) in the y direction.

The directions of shifting by the distances s1 and s2 may be opposite from those described above as far as the relation s2>s1 is satisfied. The via plugs in the first group 63f, the via plugs in the second group 63g and the via plugs in the third group 63h form respective sets, and three via plugs of each set are arranged in the x direction.

The lower-level interconnect lines 61 are designed in the form of stripes each extending in the x direction to establish electrical connection between respective sets of via plugs 63 arranged in the x direction. The first potential fixing via plug 64 is designed to be connected to the first upper-level interconnect line 62.

A test structure is actually formed based on the design of FIG. 14, as illustrated in FIGS. 15A, 15B and 15C. The test structure of FIGS. 15A, 15B and 15C will be used for the following description.

FIG. 15A shows a pattern to be tested as viewed from above the semiconductor device 508, and the voltage contrast of this pattern. FIG. 15B shows a reference pattern for comparison with the pattern to be tested as viewed from above the semiconductor device 508, and the voltage contrast of the reference pattern. FIG. 15C shows the second comparison image produced from the first comparison image resulting from the comparison between the voltage contrast of the pattern to be tested shown in FIG. 1SA and the voltage contrast of the reference pattern shown in FIG. 15B.

The pattern structure to be tested shown in FIG. 15A will be described specifically.

First, an interlayer insulation film (not shown) is deposited along the z-axis on a main surface of a silicon substrate (not shown). It will be apparent from FIG. 15A that the lower-level interconnect lines 61 in the form of stripes each extending in the x direction are formed in the interlayer insulation film. The lower-level interconnect lines 61 are arranged at the spacing t (or the longitudinal shift amount). Since the lower-level interconnect lines 61 are formed in the interlayer insulation film, the configuration of the lower-level interconnect lines 61 is shown by dotted lines.

The plurality of via plugs 63 are formed to reach the lower-level interconnect lines 61 through the surface of the interlayer insulation film (along the z-axis). The via plugs 63 are comprised of the first group 63f of via plugs, the second group 63g of via plugs and the third group 63h of via plugs which are arranged in the relationship described with reference to FIG. 14.

The first upper-level interconnect line 62 extending in the y direction is formed on the surface of the interlayer insulation film.

In the design phase, the first upper-level interconnect line 62 is designed so that the center of the diameter of the via plug 631 to be measured coincides with the central axis of the width of the first upper-level interconnect line 62. In the test structure actually formed, however, the central axis of the width of the first upper-level interconnect line 62 is deviated by the amount d in the x direction from the center of the diameter of the via plug 631. Since d'=0 is designed, the amount d of deviation corresponds to the misalignment amount.

The first potential fixing via plug 64 extends along the z-axis to establish electrical connection between the first upper-level interconnect line 62 and the silicon substrate connected to the ground. Thus, the first upper-level interconnect line 62 is connected to the ground, and the potential of the first upper-level interconnect line 62 is fixed at the ground potential. Since the first potential fixing via plug 64 underlies the first upper-level interconnect line 62, the configuration of the first potential fixing via plug 64 is shown by the dotted line.

In the above-mentioned structure, some of the via plugs in the first group 63f are shorted to the first upper-level interconnect line 62.

The voltage contrast of the pattern to be tested shown in FIG. 15A is described more specifically.

Observation of the pattern to be tested shown in FIG. 15A using the SEM image comparison type testing apparatus 500 of FIG. 1 (Step ST12) shows the following result. Regions whose potential is not fixed (i.e., sets of via plugs 63a which are not electrically connected to the first upper-level interconnect line 62) are electrically floating, and hence are positively charged when irradiated with the primary electron beam 502. This reduces the efficiency of generation of the secondary electrons 512 from the sets of via plugs 63a. Therefore, these regions are recognized as a dark contrast image.

On the other hand, regions whose potential is fixed at the ground potential (i.e., the first upper-level interconnect line 62, and sets of via plugs 63b electrically connected to the first upper-level interconnect line 62) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The reference pattern structure shown in FIG. 15B is substantially similar to the structure shown in FIG. 15A but has a difference therefrom to be described below.

The difference is that the reference pattern structure shown in FIG. 15B does not have the first potential fixing via plug 64 for fixing the first upper-level interconnect line 62 at the ground potential.

Observation of the reference pattern shown in FIG. 15B using the SEM image comparison type testing apparatus 500 of FIG. 1 (Step ST13) shows the following result. Regions whose potential is not fixed (i.e., the first upper-level interconnect line 62 and the via plugs 63) are electrically floating, and hence are positively charged when irradiated with the primary electron beam 502. This reduces the efficiency of generation of the secondary electrons 512 from the first upper-level interconnect line 62 and the via plugs 63. Therefore, these regions are recognized as a dark contrast image.

The voltage contrast is produced based on only information about the potential of the topmost surface of the semiconductor device 508.

The image comparing section 515 makes a comparison between the voltage contrasts of FIGS. 15A and 15B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 15C.

Thus, in the second comparison image shown in FIG. 15C, the first upper-level interconnect line 62 and the sets of via plugs 63b are left intact as the bright contrast regions, whereas the sets of via plugs 63a are cancelled.

Next, the contrast dimension measuring section 516 effects the clustering function to recognize the spaced contrast regions in the second comparison image of FIG. 15C as a cluster, and measures the dimensions of the cluster (Step ST15). The cluster used herein is defined to have the shape of a rectangle having a minimum size required to contain all of the contrast regions corresponding to the second group 63g of via plugs and the third group 63h of via plugs, and the contrast dimension measuring section 516 measures the dimensions of the rectangle in the x and y directions.

Thereafter, the characterizing dimension analyzing section 517 derives the actual via covering amount a and misalignment amount d of the first upper-level interconnect line 62 with respect to the patterned via plug 631 to be measured, based on the dimension measurements obtained by the contrast dimension measuring section 516 (Step ST16). A specific analysis method will be described below.

First, the misalignment amount d will be determined.

The dimension X of the cluster in the x direction is given by $$X = w + N1 \cdot s2 + b \tag{21}$$

where N1 is the number of sets of contrast regions corresponding to the via plugs as appearing in the +y direction from the via plug 631 to be measured, w is the distance between the center of the via plug 632 and the center of the via plug 633, s2 is the second lateral shift amount, and b is the diameter of the via plugs 63.

Assuming that s2>>b (which condition is easily achievable from the design point of view) in Equation (21) determines the value of N1.

$$N1 = (X - w)/s2 \tag{22}$$

Next, the dimension Y of the cluster in the y direction is given by $$Y = b + (N1 + N2) \cdot t \tag{23}$$

where N2 is the number of sets of contrast regions corresponding to the via plugs as appearing in the −y direction from the via plug 631 to be measured, and t is the longitudinal shift amount. In Equation (23), the value of N1 given by Equation (22) is used.

Assuming that t>>b (which condition is easily achievable from the design point of view) in Equation (23) determines the value of N2.

$$N2 = Y/t - (X - w)/s2 \tag{24}$$

Substituting the measurements of the dimensions X and Y of the cluster in the x and y directions obtained by the contrast dimension measuring section 516 into Equations (22) and (24) determines the values of N1 and N2 which in turn are recognized by the characterizing dimension analyzing section 517. If the values of N1 and N2 are in the form of a decimal fraction, the characterizing dimension analyzing section 517 adopts the nearest integers as N1 and N2.

By the use of the integers N1 and N2 and the first lateral shift amount si, the misalignment amount d is given by $$d = (N1 - N2) \cdot s1 \tag{25}$$

where si (<b/10) which is small is used.

Thus, the use of the integers N1 and N2 determined from Equations (22) and (24) determines the misalignment amount d from Equation (25).

On the other hand, the via covering amount a will be determined in a manner to be described below.

Assuming that the first lateral shift amount s1 is small (i.e., at least one of the via plugs 63 lined up to cross the first upper-level interconnect line 62 is approximately in contact with the first upper-level interconnect line 62), the expression b+c is given by $$b + c = (N1 + N2) \cdot s1 \tag{26}$$

where c is the width of the first upper-level interconnect line 62. Thus, substituting Equations (25) and (26) into Equation (2) determines the via covering amount a.

$$a = (N1 + N2) \cdot s1/2 \pm (N1 - N2) \cdot s1 \tag{27}$$

The condition d'=0 contemplated in the sixth preferred embodiment is taken into consideration herein. Therefore, substituting the integers N1 and N2 obtained from Equations (22) and (24) into Equation (27) determines the via covering amount a.

The characterizing dimension analyzing section 517 may previously store a correspondence table containing the dimensions X and Y of the cluster (or the integers N1 and N2) based on Equations (25) and (27), the via covering amount a and the misalignment amount d in the form of a database, thereby to automatically and rapidly derive the characterizing dimension.

As described above, the via covering amount a and the misalignment amount d are determined by measuring the dimensions of the cluster of contrast regions in the second comparison image shown in FIG. 15C. Thus, the greater the longitudinal shift amount t and the second lateral shift amount s2 are designed or the smaller the first lateral shift amount s1 is designed, the higher the accuracy of the via covering amount a and the misalignment amount d is.

In the sixth preferred embodiment, the inclination of the second imaginary line is made smaller than that of the first imaginary line (s2>s1). This expands the cluster of contrast regions in the x direction when defining the cluster of contrast regions using the clustering function, to allow the contrast regions in the x direction to be more clearly recognized, thereby facilitating the establishment of the cluster of contrast regions in the x direction. Since the contrast regions are arranged in the y direction, the cluster of contrast regions in the y direction is easily established.

Although d'=0is contemplated in the sixth preferred embodiment, the amount d' may have a finite value. This value, which is a design value and is known, is required only to be substituted into Equation (2).

<Seventh Preferred Embodiment>

A seventh preferred embodiment of the present invention is another modification of the fifth preferred embodiment. The seventh preferred embodiment is identical in the pattern to be tested which is desired to be evaluated with the fifth preferred embodiment, but is different in the reference pattern (and accordingly in the second comparison image) therefrom. A test structure shown in FIGS. 16A, 16B and 16C will be used for the following description.

FIG. 16A shows a pattern to be tested as viewed from above the semiconductor device 508, and the voltage contrast of this pattern. FIG. 16B shows a reference pattern for comparison with the pattern to be tested as viewed from above the semiconductor device 508, and the voltage contrast of the reference pattern. FIG. 16C shows the second comparison image produced from the first comparison image resulting from the comparison between the voltage contrast of the pattern to be tested shown in FIG. 16A and the voltage contrast of the reference pattern shown in FIG. 16B.

In FIGS. 16A and 16B, the reference numeral 71 designates lower-level interconnect lines; the reference characters 71*a* and 71*b* are lower-level interconnect line pieces electrically disconnected from each other; 72 designates a first upper-level interconnect line (or a linear conductor); 73 designates via plugs electrically connected to the lower-level interconnect lines 71, 71*a* or 71*b*; and 74 designates a first potential fixing via plug for fixing the potential of the first upper-level interconnect line 72.

The pattern structure to be tested and the voltage contrast thereof shown in FIG. 16A are identical with those shown in FIG. 13A, and are not particularly described. The reference numeral 731 designates a via plug to be measured (which is designed so that d'=0 in the design phase, that is, which has the diameter whose center coincides with the center of the width of the first upper-level interconnect line); 73*a* designates pairs of via plugs which are not electrically connected to the first upper-level interconnect line 72; and 73*b* designates pairs of via plugs electrically connected to the first upper-level interconnect line 72.

The reference pattern structure shown in FIG. 16B is substantially similar to the structure shown in FIG. 16A but has a difference therefrom to be described below.

The difference is that the lower-level interconnect lines 71 are replaced with the lower-level interconnect line pieces 71*a* and 71*b* electrically disconnected from each other. The disconnection is made in a manner such that two via plugs 73 of each pair are electrically independent of each other.

Observation of the reference pattern shown in FIG. 16B using the SEM image comparison type testing apparatus 500 of FIG. 1 (Step ST13) shows the following result. Regions whose potential is not fixed (i.e., via plugs 73*c* which are not electrically connected to the first upper-level interconnect line 72) are electrically floating, and hence are positively charged when irradiated with the primary electron beam 502. This reduces the efficiency of generation of the secondary electrons 512 from the via plugs 73*c*. Therefore, these regions are recognized as a dark contrast image.

On the other hand, regions whose potential is fixed at the ground potential (i.e., the first upper-level interconnect line 72, and via plugs 73*d* electrically connected to the first upper-level interconnect line 72) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The image comparing section 515 makes a comparison between the voltage contrasts of FIGS. 16A and 16B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 16C.

Thus, in the second comparison image shown in FIG. 16C, some of the pairs of via plugs 73*b* which do not correspond to the via plugs 73*d* are left intact as the bright contrast regions, whereas the first upper-level interconnect line 72, the pairs of via plugs 73*a* and the via plugs 73*d* are cancelled.

Next, the contrast dimension measuring section 516 effects the clustering function to recognize the spaced contrast regions in the second comparison image of FIG. 16C as a cluster, and measures a dimension of the cluster (Step ST15). The cluster used herein is defined to have the shape of a rectangle having a minimum size required to contain all of the contrast regions, and the contrast dimension measuring section 516 measures the dimension of the rectangle in the x direction.

Thereafter, the characterizing dimension analyzing section 517 derives the actual via covering amount a of the first upper-level interconnect line 72 with respect to the patterned via plug 731 to be measured, based on the dimension measurement obtained by the contrast dimension measuring section 516 (Step ST16). A specific analysis method will be described below.

The dimension X of the cluster in the x direction is given by $$X = N \cdot s2 + b \quad (28)$$

where N is the number of contrast regions, s2 is the second lateral shift amount, and b is the diameter of the via plugs 73.

Assuming that s2>>b (which condition is easily achievable from the design point of view) in Equation (28) determines the value of N.

$$N = X/s2 \quad (29)$$

Substituting the measurement of the dimension X of the cluster in the x direction which is obtained by the contrast dimension measuring section 516 into Equation (29) determines the value of N which in turn is recognized by the characterizing dimension analyzing section 517. If the value of N is in the form of a decimal fraction, the characterizing dimension analyzing section 517 adopts the nearest integer as N.

Assuming that the first lateral shift amount s1 is small (i.e., at least one of the via plugs 73 lined up to cross the first upper-level interconnect line 72 is approximately in contact with the first upper-level interconnect line 72), the expression b+c is given by $$b + c = N \cdot s1 \quad (30)$$

where c is the width of the first upper-level interconnect line 72.

Thus, substituting Equation (30) into Equation (2) determines the via covering amount a.

$$a = N \cdot s1/2 \pm d \quad (31)$$

The condition d'=0 contemplated in the seventh preferred embodiment is taken into consideration herein.

Therefore, substituting the integer N given by Equation (29) into Equation (31) determines the via covering amount a within the range of the misalignment amount d. The greater the second lateral shift amount s2 is designed or the smaller the first lateral shift amount s1 is designed, the higher the accuracy of the via covering amount a is.

The characterizing dimension analyzing section 517 may previously store a correspondence table containing the dimension X of the cluster (or the integer N) based on Equation (31) and the via covering amount a in the form of a database, thereby to automatically and rapidly derive the characterizing dimension.

Additionally, the seventh preferred embodiment sets the second lateral shift amount s2 at a greater value to expands the cluster of contrast regions in the x direction when defining the cluster of contrast regions using the clustering function. This makes the contrast regions more clearly to facilitate the establishment of the cluster of contrast regions in the x direction.

Although the via covering amount a is determined above by measuring the dimension of the cluster in the x direction, the via covering amount a may be determined by measuring the dimension of the cluster in the y direction.

The dimension Y of the cluster in the y direction is given by $$Y = b + N \cdot t \quad (32)$$

where t is the longitudinal shift amount.

Assuming that t>>b (which condition is easily achievable from the design point of view) in Equation (32) determines the value of N.

$$N = Y/t \quad (33)$$

Substituting Equation (33) into Equation (31) determines the via covering amount a. The greater the longitudinal shift amount t is designed, the higher the accuracy of the via covering amount a is.

The seventh preferred embodiment produces the following effect in addition to the effects of the fifth preferred embodiment. The contrast region corresponding to the first upper-level interconnect line, which has appeared in the second comparison image (FIG. 13C) of the fifth preferred embodiment, does not appear in the seventh preferred embodiment. Therefore, the seventh preferred embodiment can define the cluster of spaced contrast regions more easily.

Although d'=0 is contemplated in the seventh preferred embodiment, the amount d' may have a finite value. This value, which is a design value and is known, is required only to be substituted into Equation (2).

In the seventh preferred embodiment, each pair of via plugs are electrically disconnected from each other by separating the lower-level interconnect lines in the reference pattern. However, other methods may be used to electrically disconnect each pair of via plugs from each other in the reference pattern. An example of these methods includes dispensing with the lower-level interconnect lines themselves.

<Eighth Preferred Embodiment>

An eighth preferred embodiment of the present invention is a modification of the seventh preferred embodiment. Although the seventh preferred embodiment is not capable of determining the misalignment amount, the eighth preferred embodiment is intended to simultaneously measure the via covering amount and the misalignment amount. A test structure formed to achieve this intention is shown in FIGS. 17A, 17B and 17C.

FIG. 17A shows a pattern to be tested as viewed from above the semiconductor device 508, and the voltage contrast of this pattern. FIG. 17B shows a reference pattern for comparison with the pattern to be tested as viewed from above the semiconductor device 508, and the voltage contrast of the reference pattern. FIG. 17C shows the second comparison image produced from the first comparison image resulting from the comparison between the voltage contrast of the pattern to be tested shown in FIG. 17A and the voltage contrast of the reference pattern shown in FIG. 17B.

In FIGS. 17A and 17B, the reference numeral 81 designates lower-level interconnect lines; the reference characters 81a and 81b are lower-level interconnect line pieces electrically disconnected from each other; 82 designates a first upper-level interconnect line (or a linear conductor); 83 designates via plugs electrically connected to the lower-level interconnect lines 81, 81a or 81b; 84 designates a first potential fixing via plug for fixing the potential of the first upper-level interconnect line 82; and 831 designates a via plug to be measured which has the diameter whose center coincides with the center of the width of the first upper-level interconnect line ( d'=0) in the design phase.

The pattern structure to be tested shown in FIG. 17A will be described specifically.

The pattern structure to be tested shown in FIG. 17B is substantially similar to the pattern structure shown in FIG. 16A but has a difference to be described below.

The difference is that a third group 83*h* of via plugs spaced in the y direction are formed. The via plugs in the third group 83*h* are electrically connected to the lower-level interconnect lines 81. A first group 83*f* of via plugs (or first conductors) and a second group 83*g* of via plugs (or second conductors) are identical with those 53*f* and 53*g* of the fifth preferred embodiment, and are not particularly described.

Thus, a set of three via plugs 83 are electrically connected to each of the lower-level interconnect lines 81. A via plug 832 included in the second group 83*g* of via plugs is spaced a predetermined distance in the −x direction apart from the via plug 831 to be measured which is included in the first group 83*f* of via plugs. A via plug 833 included in the third group 83*h* of via plugs is spaced the distance w in the −x direction apart from the via plug 832. That is, w designates the center-to-center distance between the via plugs 832 and 833.

In the above-mentioned structure, some of the via plugs in the first group 83*f* are shorted to the first upper-level interconnect line 82.

The voltage contrast of the pattern to be tested shown in FIG. 17A is described more specifically.

Observation of the pattern to be tested shown in FIG. 17A using the SEM image comparison type testing apparatus 500 of FIG. 1 (Step ST12) shows the following result. Regions whose potential is not fixed (i.e., sets of via plugs 83*a* which are not electrically connected to the first upper-level interconnect line 82) are electrically floating, and hence are positively charged when irradiated with the primary electron beam 502. This reduces the efficiency of generation of the secondary electrons 512 from the sets of via plugs 83*a*. Therefore, these regions are recognized as a dark contrast image.

On the other hand, regions whose potential is fixed at the ground potential (i.e., the first upper-level interconnect line 82, and sets of via plugs 83*b* electrically connected to the first upper-level interconnect line 82) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The reference pattern structure shown in FIG. 17B is substantially similar to the structure shown in FIG. 17A but has a difference therefrom to be described below.

The difference is that the lower-level interconnect lines 81 are replaced with the lower-level interconnect line pieces 81*a* and 81*b* electrically disconnected from each other. The disconnection is made in a manner such that the first group 83*f* of via plugs and the second group 83*g* of via plugs are electrically independent of each other.

Observation of the reference pattern shown in FIG. 17B using the SEM image comparison type testing apparatus 500 of FIG. 1 (Step ST13) shows the following result. Regions whose potential is not fixed (i.e., via plugs 83*c* which are not electrically connected to the first upper-level interconnect line 82) are electrically floating, and hence are positively charged when irradiated with the primary electron beam 502. This reduces the efficiency of generation of the secondary electrons 512 from the via plugs 83*c*. Therefore, these regions are recognized as a dark contrast image.

On the other hand, regions whose potential is fixed at the ground potential (i.e., the first upper-level interconnect line 82, and via plugs 83*d* electrically connected to the first upper-level interconnect line 82) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The image comparing section 515 makes a comparison between the voltage contrasts of FIGS. 17A and 17B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 17C.

Thus, in the second comparison image shown in FIG. 17C, some of the sets of via plugs 83*b* which do not correspond to the via plugs 83*d* are left intact as the bright contrast regions, whereas the first upper-level interconnect line 82, the sets of via plugs 83*a* and the via plugs 83*d* are cancelled.

Next, the contrast dimension measuring section 516 effects the clustering function to recognize the spaced contrast regions in the second comparison image of FIG. 17C as a cluster to measure the dimensions of the cluster (Step ST15). The cluster used herein is defined to have the shape of a rectangle having a minimum size required to contain all of the contrast regions, and the contrast dimension measuring section 516 measures the dimensions of the rectangle in the x and y directions.

Thereafter, the characterizing dimension analyzing section 517 derives the actual via covering amount a and misalignment amount d of the first upper-level interconnect line 82 with respect to the patterned via plug 831 to be measured, based on the dimension measurements obtained by the contrast dimension measuring section 516 (Step ST16). A specific analysis method is identical to that of the sixth preferred embodiment, and is not particularly described.

As stated above, the eighth preferred embodiment additionally forms the third group 83*h* of via plugs to produce the following effects in addition to the effects of the seventh preferred embodiment.

One of the effects is accurate determination of the misalignment amount d and accordingly accurate determination of the via covering amount a.

Additionally, since the contrast regions are arranged in the y direction, there arises the effect of capable of simply defining the cluster in the y direction.

The characterizing dimension analyzing section 517 may previously store a correspondence table containing the dimensions of the cluster of contrast regions (or the integers based on the contrast regions), the via covering amount a and the misalignment amount d in the form of a database, thereby to automatically and rapidly derive the characterizing dimension.

In the eighth preferred embodiment, the first group 83*f* of via plugs and the second group 83*g* of via plugs are electrically disconnected from each other by separating the lower-level interconnect lines. However, other methods may be used to electrically disconnect the first and second groups 83*f* and 83*g* of via plugs from each other. An example of these methods includes dispensing with the lower-level interconnect line pieces 81*a*.

<Ninth Preferred Embodiment>

A ninth preferred embodiment of the present invention is a modification of the sixth preferred embodiment. In the ninth preferred embodiment, a plurality of insular conductors are formed in place of the third group 63*h* of via plugs formed in the sixth preferred embodiment.

Figure 18A:
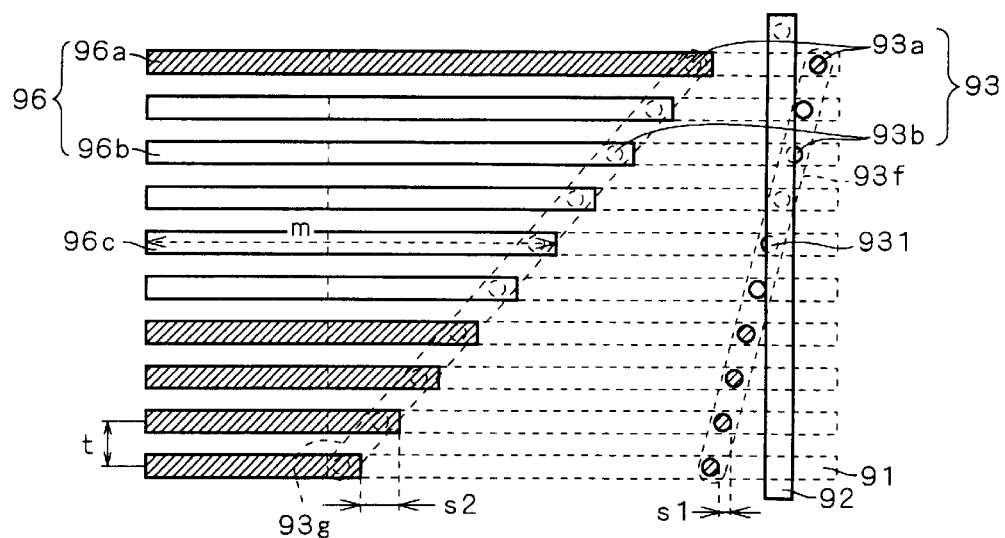
FIG. 18A shows the construction and voltage contrast of a pattern to be tested according to a ninth preferred embodiment of the present invention.
Figure 18B:
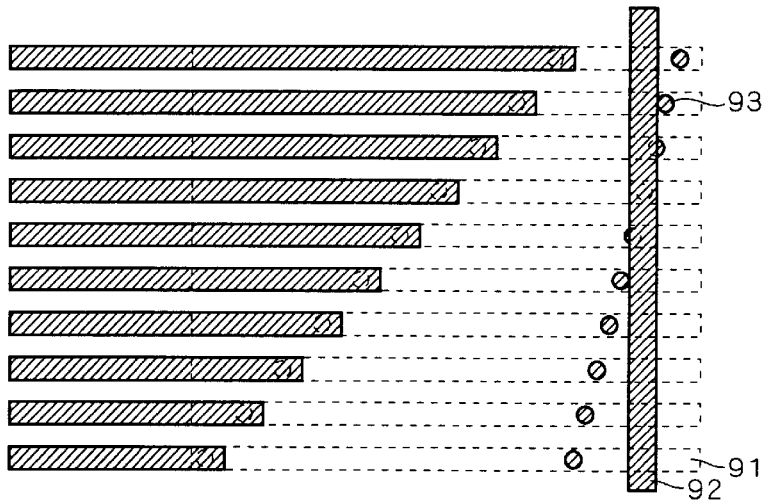
FIG. 18B shows the construction and voltage contrast of a reference pattern according to the ninth preferred embodiment.
Figure 18C:
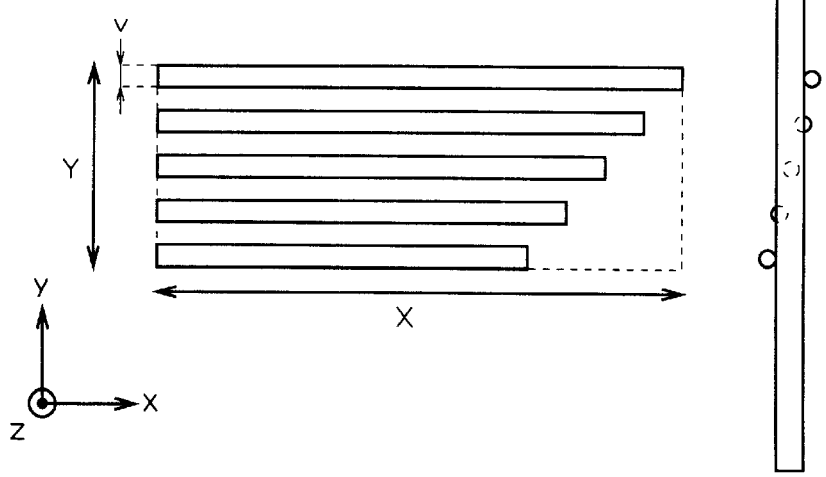
FIG. 18C shows a comparison image according to the ninth preferred embodiment.

A test structure shown in FIGS. 18A, 18B and 18C will be used for the following description. FIG. 18A shows a pattern to be tested as viewed from above the semiconductor device 508, and the voltage contrast of this pattern. FIG. 18B shows a reference pattern for comparison with the pattern to be tested as viewed from above the semiconductor device 508, and the voltage contrast of the reference pattern. FIG. 18C shows the second comparison image produced from the first comparison image resulting from the comparison between the voltage contrast of the pattern to be tested shown in FIG. 18A and the voltage contrast of the reference pattern shown in FIG. 18B.

In FIGS. 18A and 18B, the reference numeral 91 designates lower-level interconnect lines; 92 designates a first upper-level interconnect line (or a linear conductor); 93 designates via plugs electrically connected to the lower-level interconnect lines 91; 931 designates a via plug to be measured; 94 designates a first potential fixing via plug for fixing the potential of the first upper-level interconnect line 92; and 96 designates insular conductors formed in the same layer (or level) as the first upper-level interconnect line 92.

The pattern structure to be tested shown in FIG. 18A is substantially similar to the pattern structure shown in FIG. 15A but has a difference to be described below.

The difference is that the plurality of insular conductors 96 greater in area than the via plugs 93 are formed in place of the third group 63*h* of via plugs, as mentioned above. A first group 93*f* of via plugs (or first conductors), a second group 93*g* of via plugs (or second conductors), the first upper-level interconnect line 92, the lower-level interconnect lines 91, the first potential fixing via plug 94 and the like in the ninth preferred embodiment are similar in constructional relationship to corresponding components of the sixth preferred embodiment, and are not particularly described.

Specific construction of the insular conductors 96 will be described. Each of the insular conductors 96 is disposed in the form of a stripe extending in the x direction in the same layer (or level) as the first upper-level interconnect line 92. The insular conductors 96 are electrically connected to respective via plugs in the second group 93*g*. The length of and spacing between adjacent ones of the insular conductors 96 are held in a predetermined relationship. In the ninth preferred embodiment, for example, the length changes by the second lateral shift amount s2 between adjacent ones of the insular conductors 96, and the spacing between adjacent ones of the insular conductors 96 equals the longitudinal shift amount t. The insular conductors 96 are formed so as not to be shorted to the first upper-level interconnect line 92.

An insular conductor 96*c* electrically connected to a via plug paired with the via plug 931 to be measured has a length m.

The voltage contrast of the pattern to be tested shown in FIG. 18A is described more specifically.

Observation of the pattern to be tested shown in FIG. 18A using the SEM image comparison type testing apparatus 500 of FIG. 1 (Step ST12) shows the following result. Regions whose potential is not fixed (i.e., pairs of via plugs 93*a* which are not electrically connected to the first upper-level interconnect line 92, and an insular conductor 96*a* electrically connected to one of each pair of via plugs 93*a*) are electrically floating, and hence are positively charged when irradiated with the primary electron beam 502. This reduces the efficiency of generation of the secondary electrons 512 from the pairs of via plugs 93*a* and the insular conductors 96*a*. Therefore, these regions are recognized as a dark contrast image.

On the other hand, regions whose potential is fixed at the ground potential (i.e., the first upper-level interconnect line 92, pairs of via plugs 93*b* electrically connected to the first upper-level interconnect line 92, and an insular conductor 96*b* electrically connected to one of each pair of via plugs 93*b*) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The reference pattern structure shown in FIG. 18B is substantially similar to the structure shown in FIG. 18A but has a difference therefrom to be described below.

The difference is that the reference pattern structure shown in FIG. 18B does not have the first potential fixing via plug 94 for fixing the first upper-level interconnect line 92 at the ground potential.

Observation of the reference pattern shown in FIG. 18B using the SEM image comparison type testing apparatus 500 of FIG. 1 (Step ST13) shows the following result. Regions whose potential is not fixed (i.e., the first upper-level interconnect line 92, the via plugs 93, and the insular conductors 96) are electrically floating, and hence are positively charged when irradiated with the primary electron beam 502. This reduces the efficiency of generation of the secondary electrons 512 from the first upper-level interconnect line 92, the via plugs 93 and the insular conductors 96. Therefore, these regions are recognized as a dark contrast image.

The voltage contrast is produced based on only information about the potential of the topmost surface of the semiconductor device 508.

The image comparing section 515 makes a comparison between the voltage contrasts of FIGS. 18A and 18B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 18C.

Thus, in the second comparison image shown in FIG. 18C, the first upper-level interconnect line 92, the via plugs 93*b* and the insular conductors 96*b* are left intact as the bright contrast regions, whereas the insular conductors 96*a* and the via plugs 93*a* are cancelled.

Next, the contrast dimension measuring section 516 effects the clustering function to recognize the spaced contrast regions in the second comparison image of FIG. 18C as a cluster, and measures the dimensions of the cluster (Step ST15). The cluster used herein is defined to have the shape of a rectangle having a minimum size required to contain all of the contrast regions corresponding to the insular conductors 96, and the contrast dimension measuring section 516 measures the dimensions of the rectangle in the x and y directions.

Thereafter, the characterizing dimension analyzing section 517 derives the actual via covering amount a and misalignment amount d of the first upper-level interconnect line 92 with respect to the patterned via plug 931 to be measured, based on the dimension measurements obtained by the contrast dimension measuring section 516 (Step ST16). A specific analysis method will be described below.

First, the misalignment amount d will be determined.

The dimension X of the cluster in the x direction is given by $$X = m + N1 \cdot s2 \quad (34)$$

where N1 is the number of contrast regions corresponding to the insular conductors as appearing in the +y direction from the via plug 931 to be measured, m is the length of the insular conductor 96c electrically connected to the via plug 931 to be measured, and s2 is the amount of change in length between adjacent ones of the insular conductors 96.

From Equation (34), N1 is given by $$N1 = (X - m)/s2 \quad (35)$$

Next, the dimension Y of the cluster in the y direction is given by $$Y = v + (N1 + N2) \cdot t \quad (36)$$

where N2 is the number of contrast regions corresponding to the insular conductors as appearing in the −y direction from the via plug 931 to be measured, t is the longitudinal shift amount, and v is the width of each of the formed insular conductors 96 (which is a known value in the design phase). In Equation (36), the value of N1 given by Equation 35) is used.

Assuming that t>>v (which condition is easily achievable from the design point of view) in Equation (36) determines the value of N2.

$$N2 = Y/t - (X - m)/s2 \quad (37)$$

Substituting the measurements of the dimensions X and Y of the cluster in the x and y directions obtained by the contrast dimension measuring section 516 into Equations (35) and (37) determines the values of N1 and N2 which in turn are recognized by the characterizing dimension analyzing section 517. If the values of N1 and N2 are in the form of a decimal fraction, the characterizing dimension analyzing section 517 adopts the nearest integers as N1 and N2.

By the use of the integers N1 and N2 and the first lateral shift amount si, the misalignment amount d is given by $$d = (N1 \cdot N2) \cdot s1 \quad (38)$$

where si (<b/10) which is small is used.

Thus, the use of the integers N1 and N2 determined from Equations (35) and (37) determines the misalignment amount d from Equation (38).

The via covering amount a, which is derived in a manner similar to that of the sixth preferred embodiment, is not particularly described in the ninth preferred embodiment.

The characterizing dimension analyzing section 517 may previously store a correspondence table containing the dimensions X and Y of the cluster (or the integers N1 and N2), the via covering amount a and the misalignment amount d in the form of a database, thereby to automatically and rapidly derive the characterizing dimension.

As described above, the via covering amount a and the misalignment amount d are determined by measuring the dimensions of the cluster of contrast regions in the second comparison image shown in FIG. 18C. Thus, the greater the longitudinal shift amount t is designed or the smaller the first lateral shift amount s1 is designed, the higher the accuracy of the via covering amount a and the misalignment amount d is.

The ninth preferred embodiment employs the insular conductors 96 greater in area than the via plugs 93 to allow the contrast regions to be more clearly recognized, thereby facilitating the establishment of the cluster of contrast regions by using the clustering function.

Although d'=0 is contemplated in the ninth preferred embodiment, the amount d' may have a finite value. This value, which is a design value and is known, is required only to be substituted into Equation (2).

The second group 93g of via plugs are used as the via plugs electrically connected to the insular conductors 96 in the ninth preferred embodiment. However, for example, the third group 93h of via plugs, rather than the second group 93g of via plugs, may be used instead as far as they are electrically connected to the first group 93f of via plugs through the lower-level interconnect lines 91.

<Tenth Preferred Embodiment>

A tenth preferred embodiment of the present invention is intended to accurately measure a short margin between adjacent interconnect lines to conduct a test for failure between the interconnect lines. To accomplish this intention, a test structure shown in FIGS. 19A, 19B and 19C is formed. The test structure of FIGS. 19A, 19B and 19C will be used for the following description.

FIG. 19A shows a pattern to be tested as viewed from above the semiconductor device 508, and the voltage contrast of this pattern. FIG. 19B shows a reference pattern for comparison with the pattern to be tested as viewed from above the semiconductor device 508, and the voltage contrast of the reference pattern. FIG. 19C shows the second comparison image produced from the first comparison image resulting from the comparison between the voltage contrast of the pattern to be tested shown in FIG. 19A and the voltage contrast of the reference pattern shown in FIG. 19B.

In FIGS. 19A and 19B, the reference numeral 101 designates lower-level interconnect lines; 102 designates a first upper-level interconnect line (or a linear conductor); 103 designates via plugs electrically connected to the lower-level interconnect lines 101; the reference character 103f designates a first group of via plugs arranged in a uniformly spaced relationship in an imaginary line having a first inclination; 104 designates a first potential fixing via plug for fixing the potential of the first upper-level interconnect line 102; 106 designates conductors (or second conductors) formed in the same layer (or level) as the first upper-level interconnect line 102; and 107 designates second upper-level interconnect lines (or first conductors) formed in the same layer (or level) as the first upper-level interconnect line 102. The components 101 to 106 and the first group 103f of via plugs in the tenth preferred embodiment are similar in constructional relationship to the components 91 to 96 and the first group 93f of via plugs in the ninth preferred embodiment, and are not particularly described. The conductors 106 are substantially similar in construction to the insular conductors 96, but the length of the conductors 106 need not have any particular relationship.

The pattern structure to be tested shown in FIG. 19A is substantially similar to the pattern structure shown in FIG. 18A except that the second upper-level interconnect lines 107 are formed which are electrically connected to the via plugs in the first group 103f.

The second upper-level interconnect lines 107 are formed in the same layer (or level) as the first upper-level interconnect line 102 and the conductors 106, but are not connected to the conductors 106. The second upper-level interconnect lines 107 are formed individually in corresponding relation to the respective via plugs in the first group 103f. The second upper-level interconnect lines 107 have the same length in the x direction, and are arranged so that each is shifted by the first lateral shift amount s1 from its neighbor adjacent in the y direction thereto.

In the tenth preferred embodiment, the plurality of second upper-level interconnect lines 107 include a second upper-level interconnect line 107c serving as a reference line. The center of the length of the second upper-level interconnect line 107c serving as the reference line coincides with the center of the width of the first upper-level interconnect line 102.

The first upper-level interconnect line 102 and the second upper-level interconnect lines 107 may have a tapered configuration (i.e., the top width of the first upper-level interconnect line 102 is less than the bottom width thereof, and the top length of the second upper-level interconnect lines 107 is less than the bottom length thereof). It is assumed that the first and second upper-level interconnect lines 102 and 107 have such a tapered configuration in the tenth preferred embodiment.

The voltage contrast of the pattern to be tested shown in FIG. 19A is described more specifically.

Observation of the pattern to be tested shown in FIG. 19A using the SEM image comparison type testing apparatus 500 of FIG. 1 (Step ST12) shows the following result. Regions whose potential is not fixed (i.e., conductors 106a and second upper-level interconnect lines 107a which are not electrically connected to the first upper-level interconnect line 102) are electrically floating, and hence are positively charged when irradiated with the primary electron beam 502. This reduces the efficiency of generation of the secondary electrons 512 from the conductors 106a and the second upper-level interconnect lines 107a. Therefore, these regions are recognized as a dark contrast image.

On the other hand, regions whose potential is fixed at the ground potential (i.e., the first upper-level interconnect line 102, and conductors 106b and second upper-level interconnect lines 107b which are electrically connected to the first upper-level interconnect line 102) are not charged. Thus, these regions normally generate the secondary electrons 512 when irradiated with the primary electron beam 502, and are recognized as a bright contrast image.

The voltage contrast, which is produced based on only information about the potential of the topmost surface of the semiconductor device 508, reflects only information about the potentials of the first upper-level interconnect line 102, the conductors 106 and the second upper-level interconnect lines 107, and does not reflect information about the potentials of the lower-level interconnect lines 101, the via plugs 103 and the first potential fixing via plug 104.

The reference pattern structure shown in FIG. 19B is substantially similar to the structure shown in FIG. 19A but has a difference therefrom to be described below.

The difference is that the reference pattern structure shown in FIG. 19B does not have the first potential fixing via plug 104 for fixing the first upper-level interconnect line 102 at the ground potential.

Observation of the reference pattern shown in FIG. 19B using the SEM image comparison type testing apparatus 500 of FIG. 1 (Step ST13) shows the following result. Regions whose potential is not fixed (i.e., the first upper-level interconnect line 102, the conductors 106 and the second upper-level interconnect lines 107) are electrically floating, and hence are positively charged when irradiated with the primary electron beam 502. This reduces the efficiency of generation of the secondary electrons 512 from the first upper-level interconnect line 102, the conductors 106 and the second upper-level interconnect lines 107. Therefore, these regions are recognized as a dark contrast image.

The voltage contrast is produced based on only information about the potential of the topmost surface of the semiconductor device 508.

The image comparing section 515 makes a comparison between the voltage contrasts of FIGS. 19A and 19B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 19C.

Thus, in the second comparison image shown in FIG. 19C, the first upper-level interconnect line 102, the conductors 106b, and the second upper-level interconnect lines 107b are left intact as the bright contrast regions, whereas the conductors 106a and the second upper-level interconnect lines 107a are cancelled.

Next, the contrast dimension measuring section 516 effects the clustering function to recognize the spaced contrast regions in the second comparison image of FIG. 19C as a cluster, and measures a dimension of the cluster (Step ST15). The cluster used herein is defined to have the shape of a rectangle having a minimum size required to contain all of the contrast regions corresponding to the conductors 106, and the contrast dimension measuring section 516 measures the dimension of the rectangle in the y direction.

Thereafter, the characterizing dimension analyzing section 517 derives a top-to-top distance e between the patterned first and second upper-level interconnect lines 102 and 107, based on the dimension measurement obtained by the contrast dimension measuring section 516 (Step ST16). A specific analysis method will be described below.

The dimension Y of the cluster in the y direction is given by $$Y = f + (n-1) \cdot t \quad (39)$$

where n is the number of contrast regions corresponding to the conductors 106, f is the width of the conductors 106 in the y direction (which is a known value in the design phase), and t is the longitudinal shift amount.

From Equation (39), n is given by $$n = Y/t + 1 \quad (40)$$

where the relationship t>>f (which condition is easily achievable from the design point of view) is used.

Substituting the measurement of the dimension Y of the cluster in the y direction which is obtained by the contrast dimension measuring section 516 into Equation (40) determines the value of n which in turn is recognized by the characterizing dimension analyzing section 517. If the value of n is in the form of a decimal fraction, the characterizing dimension analyzing section 517 adopts the nearest integer as n.

Figure 20:
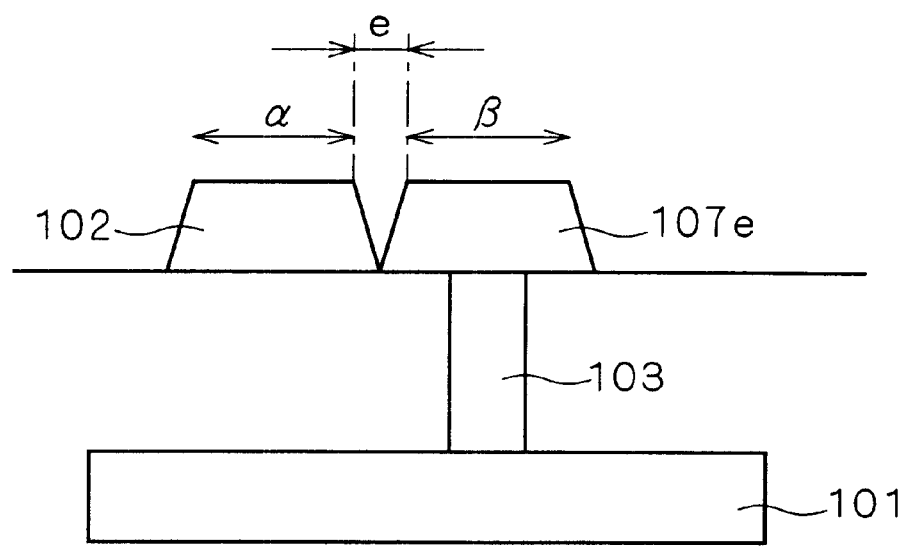
FIG. 20 shows a test structure in which a bottom end of a first upper-level interconnect line and a bottom end of a second upper-level interconnect line are in contact with each other according to the tenth preferred embodiment.

When the second upper-level interconnect lines 107 are disposed so as to be sequentially shifted by the first lateral shift amount s1 relative to each other in the x direction from the second upper-level interconnect line 107c serving as the reference line based on the assumption that the first lateral shift amount s1 is small, a second upper-level interconnect line 107e is regarded to approximately assume a position shown in FIG. 20. That is, the confronting bottom ends of the first and second upper-level interconnect lines 102 and 107e are approximately in contact with each other.

Therefore, the top-to-top distance e shown in FIG. 20 is given by $$e=(n-1)s1-(\alpha+\beta)/2 \quad (41)$$

where $\alpha$ is the top width of the first upper-level interconnect line 102, and $\beta$ is the top length of the second upper-level interconnect line 107e.

Substituting SEM measured values for $\alpha$ and $\beta$ in Equation (41) and substituting the integer obtained from Equation (40) for n determine the top-to-top distance e. The short margin between interconnect lines manufactured under the same condition is determined in the following manner.

Figure 21:
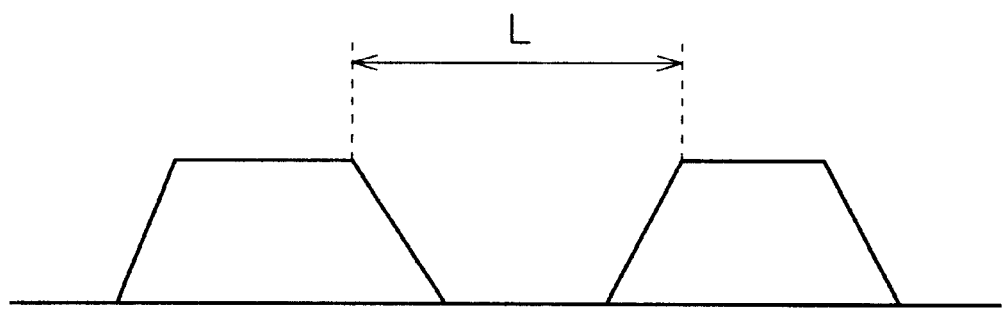
FIG. 21 is a view for determining a short margin between interconnect lines from a top-to-top distance.

When a distance between the confronting top ends of interconnect lines shown in FIG. 21 measures L, the short margin $\delta$ (or a bottom-to-bottom distance) between the interconnect lines is determined by $$\delta=L-e \quad (42)$$

The characterizing dimension analyzing section 517 may previously store a correspondence table containing the dimension Y of the cluster of contrast regions (or the integer n) based on Equation (41) and the top-to-top distance e in the form of a database, thereby to automatically and rapidly derive the characterizing dimension.

The above-mentioned method effects the clustering function to recognize the rectangle having the minimum size required to contain all of the contrast regions corresponding to the conductors 106 in the second comparison image of FIG. 19C, to measure the dimension of the rectangle in the y direction, thereby determining the top-to-top distance e based on the dimension of the rectangle in the y direction. However, the same clustering function may be used to recognize the minimum distance in the x direction which is required to contain all of the contrast regions corresponding to the second upper-level interconnect lines 107, to measure the distance in the x direction, thereby determining the top-to-top distance e.

Assuming the first lateral shift amount s1 is small, the above-mentioned minimum distance (or dimension) X in the x direction is given by $$X=s+(n-1)\cdot s1 \quad (43)$$

Substituting the measured dimension X in the x direction and the SEM measured value of the top length $\beta$ of the second upper-level interconnect lines 107 into Equation (43) determines the value of n.

$$n=(X-f)/s1+1 \quad (44)$$

If the value of n calculated from Equation (44) is in the form of a decimal fraction, the nearest integer is taken as n. The subsequent procedure is similar to that discussed above, and is not particularly described.

As described above, the short margin between interconnect lines of the tapered configuration or a damascene configuration which has not been measurable in the background art techniques is determined indirectly from the top-to-top distance e by measuring the dimension of the cluster of contrast regions in the second comparison image shown in FIG. 19C. Thus, the greater the longitudinal shift amount t is designed or the smaller the first lateral shift amount s1 is designed, the higher the accuracy of the short margin between the interconnect lines is.

Although the conductors 106 are used for the test, the conductors 106 need not be used. The effects of the tenth preferred embodiment are sufficiently achieved if there are provided a plurality of via plugs electrically connected to the via plugs in the first group and arranged in a uniformly spaced relation in the y direction. However, the tenth preferred embodiment employs the conductors 106 having a greater area, to allow the contrast regions corresponding to the conductors 106 to be more clearly recognized than those corresponding to the via plugs, thereby facilitating the establishment of the cluster of contrast regions by using the clustering function.

<Eleventh Preferred Embodiment>

An eleventh preferred embodiment of the present invention is a modification of the tenth preferred embodiment. The eleventh preferred embodiment is intended to remove the contrast regions corresponding to the first and second upper-level interconnect lines from the second comparison image shown in FIG. 19C to facilitate the clustering process.

Figure 22:
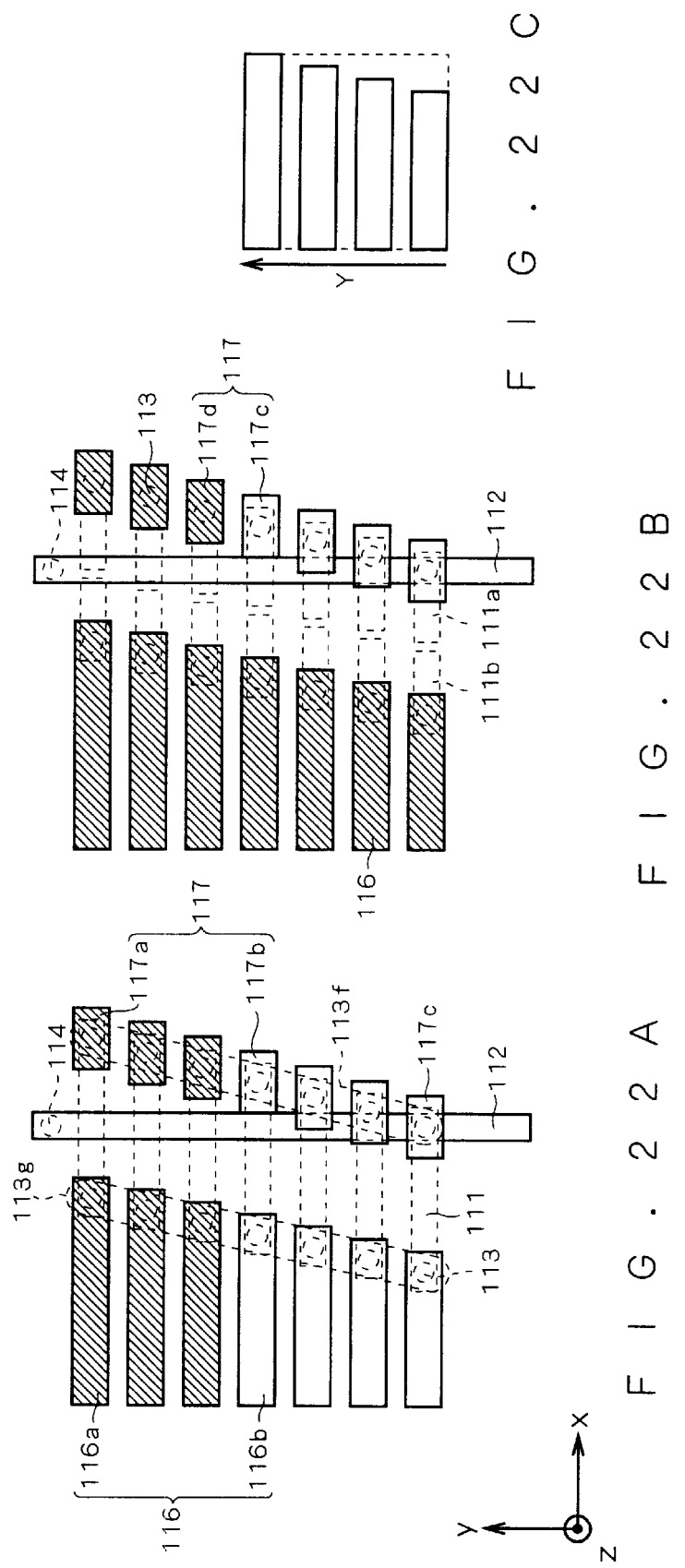
FIG. 22A shows the construction and voltage contrast of a pattern to be tested according to an eleventh preferred embodiment of the present invention.
FIG. 22B shows the construction and voltage contrast of a reference pattern according to the eleventh preferred embodiment.
FIG. 22C shows a comparison image according to the eleventh preferred embodiment.
Figure 23:
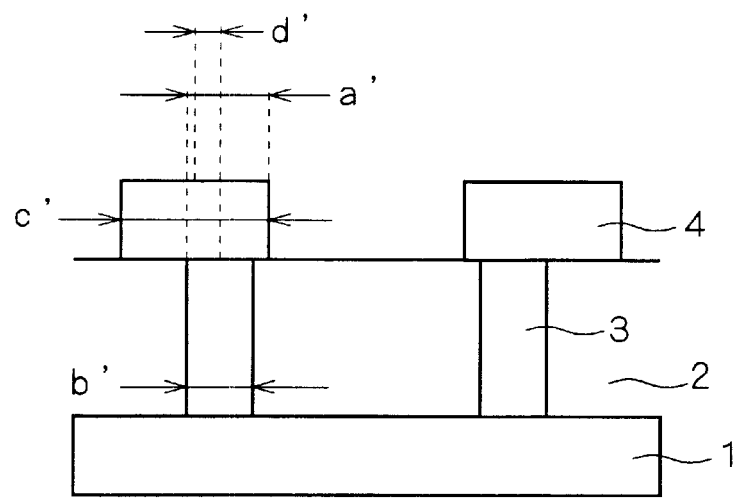
FIG. 23 is a sectional view of a semiconductor device designed to determine characterizing dimensions in the background art.
Figure 24:
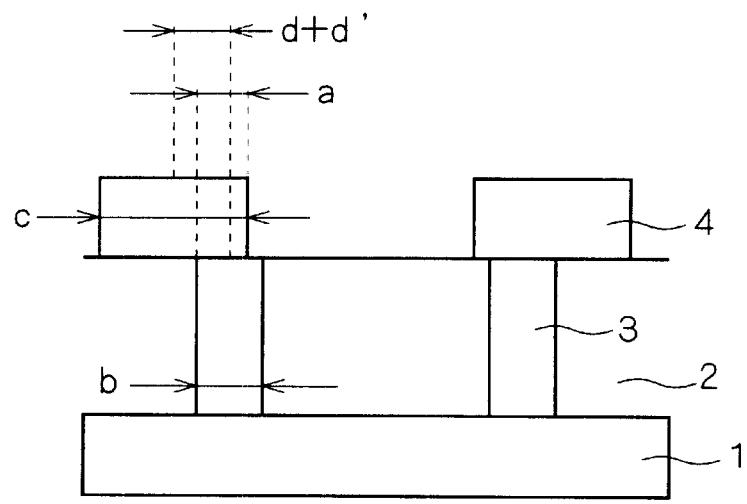
FIG. 24 is a sectional view of a semiconductor device actually manufactured based on the design of FIG. 23.
Figure 25:
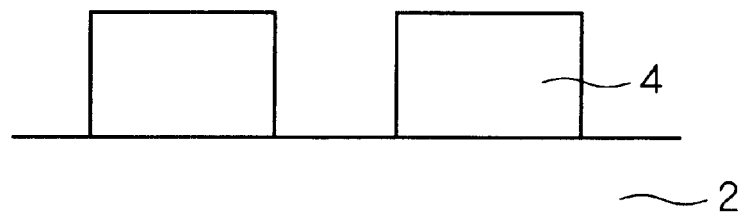
FIG. 25 shows interconnect lines as formed having a uniform width.
Figure 26:
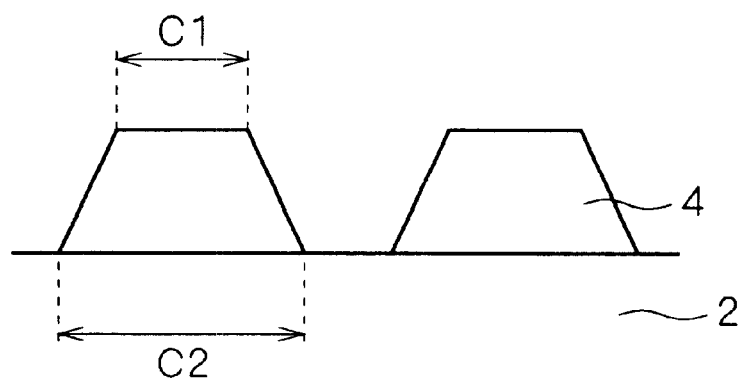
FIG. 26 shows interconnect lines as formed having a tapered structure.
Figure 27:
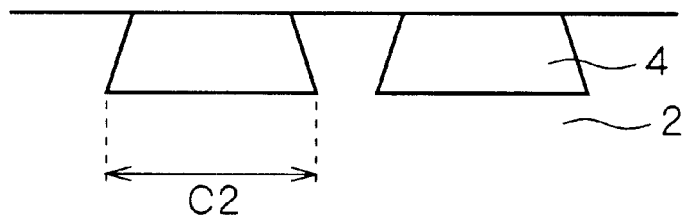
FIG. 27 shows interconnect lines as formed having a damascene structure.

A test structure shown in FIGS. 22A, 22B and 22C will be used for the following description. FIG. 22A shows a pattern to be tested as viewed from above the semiconductor device 508, and the voltage contrast of this pattern. FIG. 22B shows a reference pattern for comparison with the pattern to be tested as viewed from above the semiconductor device 508, and the voltage contrast of the reference pattern. FIG. 22C shows the second comparison image produced from the first comparison image resulting from the comparison between the voltage contrast of the pattern to be tested shown in FIG. 22A and the voltage contrast of the reference pattern shown in FIG. 22B.

In FIGS. 22A and 22B, the reference numeral 111 designates lower-level interconnect lines; the reference characters 111a and 111b designate lower-level interconnect line pieces; 112 designates a first upper-level interconnect line (or a linear conductor); 113 designates via plugs electrically connected to the lower-level interconnect lines 111; 113f designates a first group of via plugs arranged in a uniformly spaced relationship in a first imaginary line having a first inclination; 113g designates a second group of via plugs arranged in a uniformly spaced relationship in a second imaginary line having a second inclination; 114 designates a first potential fixing via plug for fixing the potential of the first upper-level interconnect line 112; 116 designates conductors (or second conductors) formed in the same layer (or level) as the first upper-level interconnect line 112; and 117 designates second upper-level interconnect lines (or first conductors) formed in the same layer (or level) as the first upper-level interconnect line 112.

The components 111 to 117 and the first group 113f of via plugs in the eleventh preferred embodiment are similar in constructional relationship to the components 101 to 107 and the first group 103f of via plugs in the tenth preferred embodiment, but differ therefrom in construction in the reference pattern. The via plugs in the first group 113f and the via plugs in the second group 113g form respective pairs. In the eleventh preferred embodiment, the second inclination is not particularly limited as far as the via plugs in the second group 113g are arranged in the y direction in a uniformly spaced relationship.

The reference pattern of FIG. 22B differs from the reference pattern of FIG. 19B of the tenth preferred embodiment in that the first potential fixing via plug 114 is formed for fixing the potential of the first upper-level interconnect line 102 and in that each pair of via plugs 113 are electrically disconnected from each other. In the reference pattern of FIG. 22B, the method of electrically disconnecting each pair of via plugs 113 from each other is carried out by separating the lower-level interconnect lines into the lower-level interconnect line pieces 111a and 111b. However, the second group 113g of via plugs, for example, may be dispensed with if the second upper-level interconnect lines 117 are electrically disconnected from the conductors 116.

Observation of the reference pattern shown in FIG. 22B using the SEM image comparison type testing apparatus 500 of FIG. 1 (Step ST13) shows the following result. Regions whose potential is not fixed (i.e., the conductors 116, and second upper-level interconnect lines 117d which are not electrically connected to the first upper-level interconnect line 112) are electrically floating, and hence are positively charged when irradiated with the primary electron beam 502. This reduces the efficiency of generation of the secondary electrons 512 from the conductors 116 and the second upper-level interconnect lines 117d. Therefore, these regions are recognized as a dark contrast image.

On the other hand, regions whose potential is fixed at the ground potential (i.e., the first upper-level interconnect line 112, and second upper-level interconnect lines 117c electrically connected to the first upper-level interconnect line 112) are not charged. Thus, these regions normally generate the secondary electrons 512 when irradiated with the primary electron beam 502, and are recognized as a bright contrast image.

The voltage contrast is produced based on only information about the potential of the topmost surface of the semiconductor device 508.

The pattern to be tested shown in FIG. 22A is identical in construction with the pattern shown in FIG. 19A, and is not particularly described.

Thus, the voltage contrast shown in FIG. 22A is such that regions whose potential is not fixed (i.e., conductors 116a and second-upper level interconnect lines 117a which are not connected to the first upper-level interconnect line 112) are recognized as a dark contrast image, whereas regions whose potential is fixed (i.e., the first upper-level interconnect line 112, and conductors 116b and second upper-level interconnect lines 117b which are electrically connected to the first upper-level interconnect line 112) are recognized as a bright contrast image.

The image comparing section 515 makes a comparison between the voltage contrasts of FIGS. 22A and 22B thus obtained (Step ST14). This comparison is made by obtaining a contrast difference therebetween. Specifically, as a result of comparison, a region which appears as a bright contrast region (or dark contrast region) in both of the voltage contrasts of the pattern to be tested and the reference pattern is cancelled. If a region differs in contrast between the voltage contrasts (i.e., bright in one of the voltage contrasts and dark in the other), the region in the voltage contrast of the pattern to be tested is left intact. This is shown in FIG. 22C.

Thus, in the second comparison image shown in FIG. 22C, the conductors 116b are left intact as the bright contrast regions, whereas the first upper-level interconnect line 112, the conductors 116a and the second upper-level interconnect lines 117 are cancelled.

Next, the contrast dimension measuring section 516 effects the clustering function to recognize the contrast regions in the second comparison image of FIG. 22C as a cluster, and measures a dimension of the cluster (Step ST15). The cluster used herein is defined to have the shape of a rectangle having a minimum size required to contain all of the contrast regions corresponding to the conductors 116, and the contrast dimension measuring section 516 measures the dimension of the rectangle in the y direction.

Thereafter, the characterizing dimension analyzing section 517 derives the top-to-top distance e between the patterned first and second upper-level interconnect lines 112 and 117, based on the dimension measurement obtained by the contrast dimension measuring section 516 (Step ST16).

Consequently, the short margin between interconnect lines manufactured under the same condition is determined by obtaining the top-to-top distance e. A specific analysis method therefore in the eleventh preferred embodiment is identical with that in the tenth preferred embodiment, and is not particularly described.

The above-mentioned process in the eleventh preferred embodiment removes the contrast regions corresponding to the first and second upper-level interconnect lines 112 and 117 as indicated in the second comparison image (FIG. 22C), to allow the characteristic contrast regions to be easily recognized as a cluster by the use of the clustering function.

While the invention has been described in detail, the foregoing description is in all aspects illustrative and not restrictive. It is understood that numerous other modifications and variations can be devised without departing from the scope of the invention.

What is claimed is:

1. A method of testing a semiconductor device being manufactured on a semiconductor substrate by detecting secondary electrons produced by irradiation of a predetermined region with a primary electron beam and using a voltage contrast produced based on the intensity of said secondary electrons, said method comprising the steps of:
   (a) preparing a predetermined pattern to be tested;
   (b) preparing a reference pattern similar in construction to said predetermined pattern;
   (c) producing said voltage contrast of said predetermined pattern;
   (d) producing said voltage contrast of said reference pattern;
   (e) making a comparison between said voltage contrast of said predetermined pattern and said voltage contrast of said reference pattern to produce a first comparison image, and binarizing said first comparison image;
   (f) producing a second comparison image containing only one of two binary contrast levels resulting from the binarization in said step (e);
   (g) measuring a dimension based on said second comparison image; and
   (h) determining a characterizing dimension varying depending on the process of manufacture of said semiconductor device from a result of measurement in said step (g).

2. The method according to claim 1, wherein
said predetermined pattern prepared in said step (a) includes
   a linear conductor maintained at a fixed potential, and
   a plurality of first conductors arranged in a uniformly spaced relationship in a first imaginary line crossing said linear conductor and having a first inclination.

3. The method according to claim 2, wherein
said predetermined pattern prepared in said step (a) further includes
   a plurality of second conductors arranged in a predetermined spaced relationship in a longitudinal direction of said linear conductor, and
   said plurality of first conductors are electrically connected to said plurality of second conductors, respectively.

4. The method according to claim 3, wherein
said predetermined pattern prepared in said step (a) has a plurality of via plugs including a first group of via plugs, and a second group of via plugs arranged in a predetermined spaced relationship in a second imaginary line having a second inclination, said first group of via plugs being said plurality of first conductors, said second group of via plugs being said plurality of second conductors.

5. The method according to claim 4, wherein
said first inclination and said second inclination in said predetermined pattern prepared in said step (a) have the same magnitude and opposite directions, and
said reference pattern prepared in said step (b) is not maintained at any fixed potential.

6. The method according to claim 4, wherein
said first inclination and said second inclination in said predetermined pattern prepared in said step (a) have the same magnitude and the same direction, and
said reference pattern prepared in said step (b) is maintained at said fixed potential.

7. The method according to claim 6, wherein
said first group of via plugs and said second group of via plugs in said predetermined pattern prepared in said step (a) are electrically connected to each other to form respective pairs of via plugs, and
said pairs of via plugs include one pair of via plugs maintained at said fixed potential.

8. The method according to claim 4, wherein
said first inclination and said second inclination in said predetermined pattern prepared in said step (a) differ in magnitude from each other, and
said reference pattern prepared in said step (b) is not maintained at any fixed potential.

9. The method according to claim 4, wherein
said first inclination and said second inclination in said predetermined pattern prepared in said step (a) differ in magnitude from each other, and
a pattern corresponding to said linear conductor in said reference pattern prepared in said step (b) is maintained at said fixed potential, and patterns corresponding to said first group of via plugs and said second group of via plugs in said reference pattern prepared in said step (b) are electrically independent of each other.

10. The method according to claim 8, wherein
said plurality of via plugs in said predetermined pattern prepared in said step (a) further includes a third group of via plugs arranged in a uniformly spaced relationship in the longitudinal direction of said linear conductor, and
corresponding ones of said first, second and third groups of via plugs are electrically connected to one another.

11. The method according to claim 9, wherein
said plurality of via plugs in said predetermined pattern prepared in said step (a) further includes a third group of via plugs arranged in a uniformly spaced relationship in the longitudinal direction of said linear conductor, and
corresponding ones of said first, second and third groups of via plugs are electrically connected to one another.

12. The method according to claim 4, wherein
said step (a) includes the step of forming a plurality of insular conductors, said plurality of insular conductors being connected to said plurality of via plugs, respectively, but not being connected to said linear conductor, said plurality of insular conductors having the same width in the longitudinal direction of said linear conductor, said plurality of insular conductors being greater in area than said plurality of via plugs.

13. The method according to claim 12, wherein
said plurality of insular conductors formed in said step (a) have respective lengths changing based on a predetermined rule.

14. The method according to claim 3, wherein
said plurality of second conductors in said predetermined pattern prepared in said step (a) have the same width in the longitudinal direction of said linear conductor, and
said reference pattern prepared in said step (b) is not maintained at any fixed potential.

15. The method according to claim 3, wherein
said plurality of second conductors in said predetermined pattern prepared in said step (a) have the same width in the longitudinal direction of said linear conductor, and
a pattern corresponding to said linear conductor in said reference pattern prepared in said step (b) is maintained at said fixed potential, and patterns corresponding to said first and second conductors in said reference pattern prepared in said step (b) are electrically independent of each other.

16. The method according to claim 1, wherein
said step (g) includes the step of recognizing contrast regions spaced in said second comparison image as a cluster to measure a dimension of said cluster.

17. The method according to claim 1, wherein
said characterizing dimension is determined based on a previously prepared correspondence table in said step (h).

18. The method according to claim 3, wherein
said plurality of second conductors in said predetermined pattern prepared in said step (a) are disposed in such a manner that a longitudinal shift amount defined as a distance between adjacent ones of said second conductors in said longitudinal direction of said linear conductor is greater than the width of said second conductors in said longitudinal direction of said linear conductor.

19. The method according to claim 2, wherein
said plurality of first conductors in said predetermined pattern prepared in said step (a) are disposed in such a manner that a lateral shift amount defined as a distance between adjacent ones of said first conductors in a direction perpendicular to said longitudinal direction of said linear conductor is less than one-tenth the size of said first conductors.

* * * * *